(12) United States Patent  (10) Patent No.: US 8,157,726 B2
Melder  (45) Date of Patent: Apr. 17, 2012

(54) ENDOSCOPIC IMAGING SYSTEM

(75) Inventor: Patrick C. Melder, Clarksburg, MD (US)

(73) Assignee: Envisionier Medical Technologies LLC, Rockville, MD (US)

( * ) Notice: Subject to any disclaimer, the term of this patent is extended or adjusted under 35 U.S.C. 154(b) by 1329 days.

(21) Appl. No.: 11/768,965

(22) Filed: Jun. 27, 2007

(65) Prior Publication Data

US 2007/0276183 A1    Nov. 29, 2007

Related U.S. Application Data

(63) Continuation-in-part of application No. PCT/US2005/047281, filed on Dec. 28, 2005.

(60) Provisional application No. 60/639,451, filed on Dec. 28, 2004.

(51) Int. Cl.
*A61B 1/04* (2006.01)
*A61B 1/00* (2006.01)

(52) U.S. Cl. ........................................ 600/112; 600/101

(58) Field of Classification Search .............. 348/84–85; 600/101–102, 112, 132
See application file for complete search history.

(56) References Cited

U.S. PATENT DOCUMENTS

| | | | |
|---|---|---|---|
| 4,607,622 A | 8/1986 | Fritch et al. |
| 4,633,304 A | 12/1986 | Nagasaki |
| 4,646,724 A | 3/1987 | Sato et al. |
| 4,663,657 A | 5/1987 | Nagasaki et al. |
| 4,682,586 A | 7/1987 | Matsuo |
| 4,696,544 A | 9/1987 | Costella |
| 4,712,133 A | 12/1987 | Kikuchi |
| 4,719,508 A | 1/1988 | Sasaki et al. |
| 4,756,304 A | 7/1988 | Watanabe |
| 4,807,594 A | 2/1989 | Chatenever |
| 4,844,071 A | 7/1989 | Chen et al. |
| 4,860,732 A | 8/1989 | Hasegawa et al. |
| 4,884,134 A | 11/1989 | Tsuji et al. |
| 4,947,245 A | 8/1990 | Ogawa et al. |
| 5,005,943 A | 4/1991 | Fort |

(Continued)

OTHER PUBLICATIONS

Han Lien International Co. Brochure, Taiwan, undated.

(Continued)

*Primary Examiner* — Philip R Smith
(74) *Attorney, Agent, or Firm* — Gianna Julian-Arnold; Saul Ewing LLP

(57) ABSTRACT

A portable hand-held endoscopy system adapted for interchangeable use with a variety of endoscopes. The system includes an endoscope having a first end and a second end, the first end having an eyepiece and the second end having a viewing end, the endoscope further having a coupler for coupling to a light source; and a battery operated unitary digital camera having an optical input, viewing screen, digital signal processor, memory with embedded software for processing data from the processor and for displaying an image on the viewing screen, and a coupler having a first end and a second end, wherein the first end includes a connector for removably connecting to the eyepiece, and the second end is coupled to the optical input of the digital camera. The video display is rotatable and pivotable about several different axes of rotation and a pivot point spaced distally from the main camera body. An ergonomic camera housing is provided, including a bulbous gripping region and two opposing forefinger accepting regions, facilitating a trigger-like grip and use of the camera by a physician. Redundant controls for moving video and still image capture facilitate ease of use by the physician as the camera and associated endoscope are held in a variety of orientations.

21 Claims, 24 Drawing Sheets

U.S. PATENT DOCUMENTS

| | | | |
|---|---|---|---|
| 5,188,093 | A | 2/1993 | Lafferty et al. |
| 5,199,417 | A | 4/1993 | Muller et al. |
| 5,349,942 | A | 9/1994 | Heimberger |
| 5,392,067 | A | 2/1995 | Konno et al. |
| 5,411,500 | A | 5/1995 | Lafferty et al. |
| 5,573,492 | A | 11/1996 | Dianna et al. |
| 5,808,813 | A | 9/1998 | Lucey et al. |
| 5,841,373 | A * | 11/1998 | Mason ............................ 341/21 |
| 5,846,185 | A | 12/1998 | Carollo et al. |
| 5,865,727 | A | 2/1999 | Sano et al. |
| 5,873,814 | A | 2/1999 | Adair |
| 5,879,289 | A | 3/1999 | Yarush et al. |
| 5,891,013 | A | 4/1999 | Thompson |
| 5,898,165 | A | 4/1999 | Kinugasa et al. |
| 6,007,485 | A | 12/1999 | Koeda et al. |
| 6,033,360 | A | 3/2000 | Sano et al. |
| 6,186,944 | B1 | 2/2001 | Tsai |
| 6,224,544 | B1 | 5/2001 | Takada |
| 6,361,489 | B1 | 3/2002 | Tsai |
| 6,432,046 | B1 | 8/2002 | Yarush et al. |
| 6,468,202 | B1 * | 10/2002 | Irion et al. .................... 600/117 |
| 6,500,115 | B2 | 12/2002 | Krattiger et al. |
| 6,626,825 | B2 | 9/2003 | Tsai |
| 6,712,760 | B2 | 3/2004 | Sano et al. |
| 6,809,499 | B2 | 10/2004 | Solingen |
| 6,832,986 | B2 | 12/2004 | Chhibber et al. |
| 6,863,651 | B2 | 3/2005 | Remijan et al. |
| 6,878,108 | B2 | 4/2005 | Ouchi |
| 6,899,673 | B2 | 5/2005 | Ogura et al. |
| 6,919,914 | B2 | 7/2005 | Beutter et al. |
| 7,137,948 | B2 | 11/2006 | Tsai |
| 2001/0025174 | A1 | 9/2001 | Daniel et al. |
| 2002/0011544 | A1 * | 1/2002 | Bosson ........................ 248/121 |
| 2003/0050534 | A1 | 3/2003 | Kazakevich |
| 2003/0060226 | A1 * | 3/2003 | Abood et al. ................. 455/550 |
| 2003/0078476 | A1 | 4/2003 | Hill |
| 2003/0086240 | A1 * | 5/2003 | Jobs et al. ..................... 361/683 |
| 2003/0092965 | A1 | 5/2003 | Konomura et al. |
| 2003/0122927 | A1 | 7/2003 | Saito et al. |
| 2003/0174205 | A1 | 9/2003 | Amling et al. |
| 2004/0019255 | A1 | 1/2004 | Sakiyama |
| 2004/0186345 | A1 | 9/2004 | Yang et al. |
| 2004/0204628 | A1 * | 10/2004 | Rovegno ....................... 600/131 |
| 2004/0215057 | A1 | 10/2004 | Wellman et al. |
| 2005/0140191 | A1 * | 6/2005 | Curran et al. ............... 297/217.3 |

OTHER PUBLICATIONS

Mega Medical Catalogue, Jun. 24, 2004, South Korea.

PCT International Search Report in connection with PCT/US2005/047281, filed on Dec. 28, 2005, mailed on Jun. 1, 2007.

Co-pending design U.S. Appl. No. 29/247,639, filed Jun. 30, 2006, Entitled Camera, and having common inventors and assignee with the present application.

PCT International Preliminary Report on Patentability in connection with PCT/US2005/047281, filed on Dec. 28, 2005, mailed on Jul. 12, 2007.

* cited by examiner

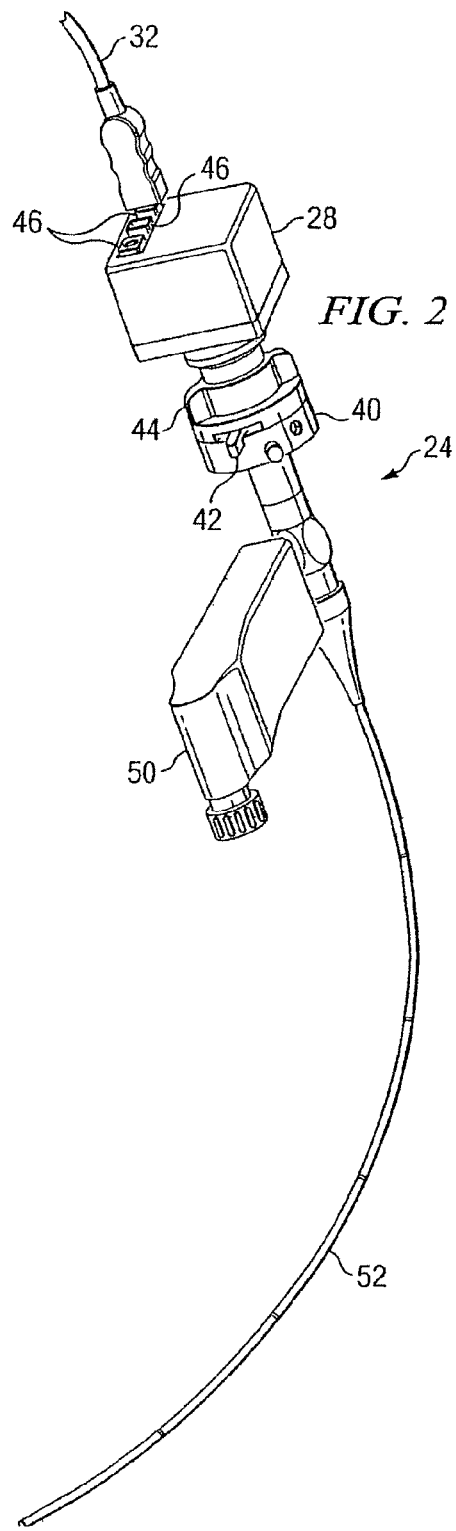
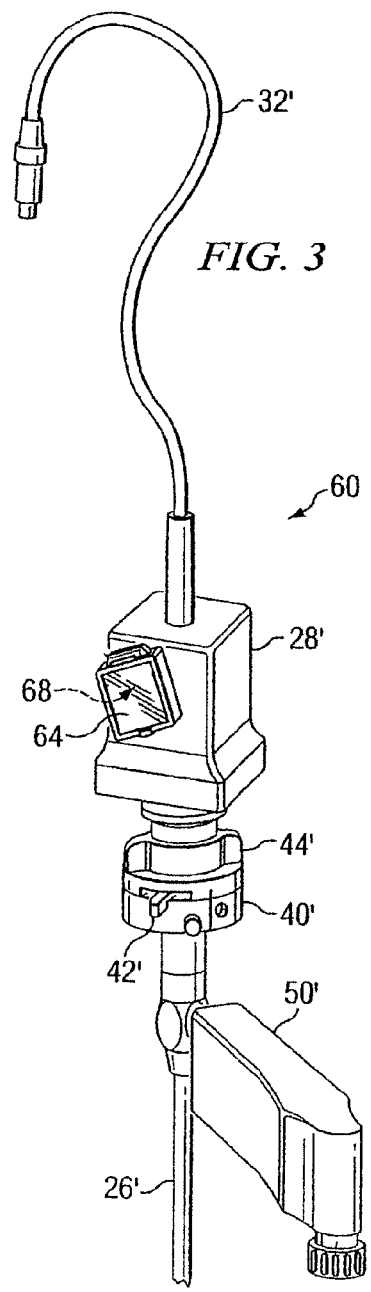
FIG. 2
FIG. 3

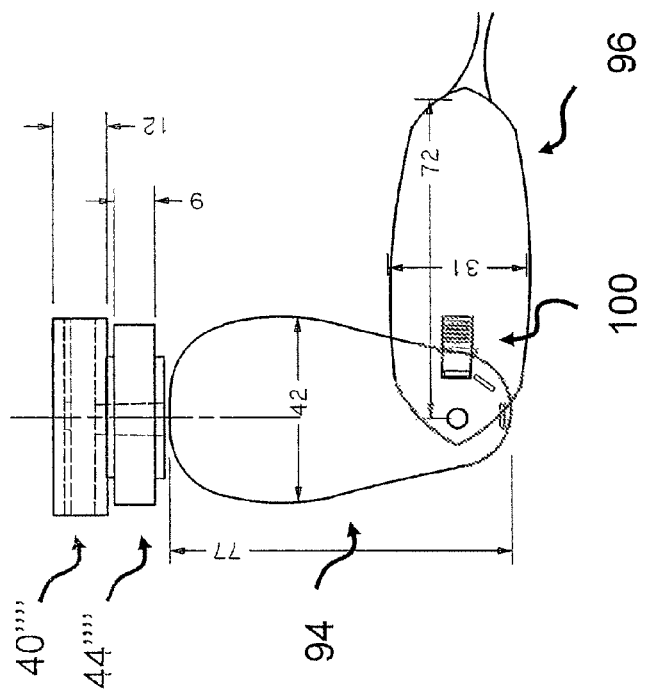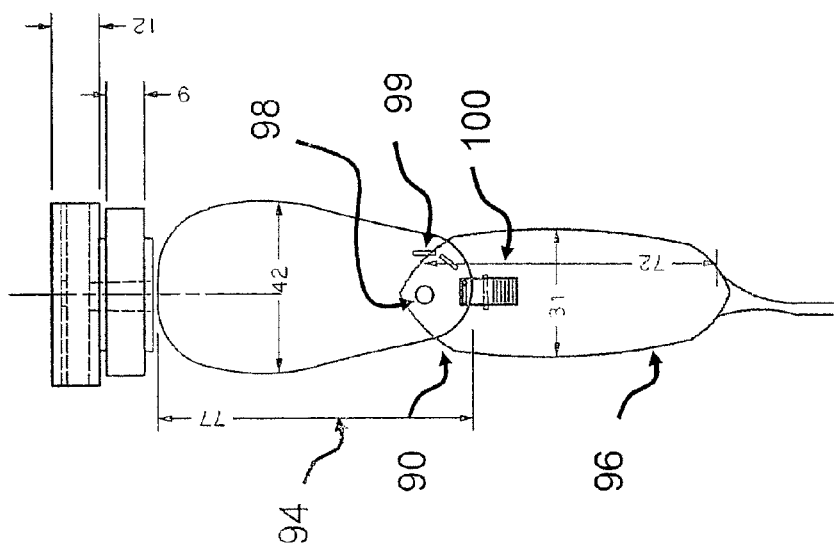

ENDOSCOPIC IMAGING SYSTEM

CROSS-REFERENCE TO RELATED APPLICATIONS

This application is a continuation in part of International Patent Application No. PCT/US2005/047281, filed Dec. 28, 2005, the entirety of which is hereby incorporated by reference, which claims the benefit of U.S. Provisional Application No. 60/639,451, filed Dec. 28, 2004, the entirety of which is hereby incorporated by reference. This application also claims priority to U.S. Design patent application Ser. No. 29/247,639, filed Jun. 30, 2006.

BACKGROUND OF THE INVENTION

1. Field of the Invention

This invention relates generally to endoscopic imaging, and more particularly to an endoscopic imaging system that is adaptable to any endoscope, is less expensive, and is more mobile and portable than the current systems available to physicians.

2. Background Art

As is well known, various technologies are available to the medical profession for use in viewing and imaging internal organs and systems of the human body. For example, otolaryngologists often require an endoscopic examination of the patient's upper respiratory system. One of the most common tools used by otolaryngologists to view the upper respiratory system is an endoscope. Similarly, endoscopes are used by surgeons and physicians in many fields of medicine in order to view parts of the human body internally for examination, diagnosis, and treatment. Initially, endoscopes included only an eyepiece, through which the physician could view the area being examined and/or treated. However, modernization of medical tools have produced more modern endoscopic systems that include camera assemblies with a camera head attached to the proximal end or eyepiece of the endoscope, typically via a coupler. For example, U.S. Pat. No. 4,697,894 issued to Takamura et al and discloses a connection device for connecting an associated unit to an eyepiece section of an endoscope. U.S. Pat. No. 4,697,894 is incorporated herein by reference.

Visual documentation is important in medicine, particularly for improved patient care and educational and training purposes. There are several variations of camera systems available to physicians that attach to the endoscope for imaging what the endoscope is viewing. For still photography a 35 mm analog single lens reflex (SLR) camera or a modern digital (SLR and non-SLR) camera can be used. For video photography a camera head, camera control unit, adapters to fit the endoscope onto the camera, and a video system monitor are used for viewing. All methods of endoscopy require a light source for illumination. These systems are commonly used in doctor's offices, emergency rooms, hospital rooms, and operating rooms, but are very expensive, not easily adapted, and not configured to be easily transported between and among multiple locations.

The cameras currently available to medical professionals are not easily configured for endoscopic imaging. A camera control unit is required to control the camera and process the digital or analog image signals received by the camera from the endoscope. Analog images are processed through an analog/digital converter and transmitted as a digital image. Digital images are captured directly to a charged coupled device (CCD) that captures images in pixel format as an electrical charge. This information is then processed with a varying array of filters to produce color images. The images must then be transmitted to a computing device for storage, editing, and further processing of the data.

The camera control unit and accompanying computer and viewing screen are bulky, heavy, and not easily transported to different locations. In addition to the size and transport limitations, the systems currently available can range in cost from $10,000 or more for just the camera and camera control unit. In addition to the cost of the camera and camera control unit, the endoscope, and typically a light source must be purchased.

Manufacturers have attempted to produce digital archiving platforms to allow easy integration into the digital age by integrating disc burners and hard drives into the endoscopy units so that exams can be stored directly onto removable media. These alternatives, however, limit editing of the images and are not very dynamic. Other manufacturers have attempted to produce endoscopy units that capture the images directly into a proprietary computer system designed for the specific function of video capturing and archiving. These systems provide better data manipulation, but can cost more than $20,000, and thus not affordable for a small or cost-limited practice.

Some alternative systems have been designed with portable components. These portable component systems are smaller in size than the fixed systems, but still require a camera control unit, a monitor, a means for capturing the images, and a light source in addition to the main components of a camera and endoscope. Although these systems are classified as portable, they are heavy, cumbersome, and expensive. U.S. Pat. No. 6,432,046 issued to Yarush et al and discloses a hand-held portable camera for producing video images of an object, and has as an object to provide a camera which features a lighting system capable of high-intensity illumination without creating an over abundance of heat. Yarush et al discloses a fixed lens tube which receives a variety of apparently custom probes and, in certain embodiments, further requires one of several adapters to receive certain probes. Additionally, this aforementioned patent is not readily adapted to the standard fittings of the eyepiece of endoscopes used in medical practices.

BRIEF SUMMARY OF THE INVENTION

The present invention comprises an endoscopic imaging system which overcomes the foregoing and other difficulties. In one embodiment, the present invention provides a portable hand-held endoscopy system adapted for interchangeable use with a variety of endoscopes. The system includes an endoscope having a first end and a second end, the first end having an eyepiece and the second end having a viewing end, a battery operated digital camera having an optical input, viewing screen, digital signal processor and memory with embedded software for processing data from the processor and for displaying an image on the viewing screen, and a coupler having a first end and a second end, wherein the first end includes a connector for removably connecting to the eyepiece, and the second end includes a connector for coupling to the optical input of the digital camera.

In another embodiment, the system may not include the viewing screen. Alternatively, or in addition, the system may include features to provide a high speed digital data transfer protocol port for coupling to an external device, such as a personal computing device.

In another embodiment, the present invention provides a portable hand-held endoscopy system adapted for interchangeable use with a variety of endoscopes. The system having an endoscope having a first end and a second end, the first end having an eyepiece and the second end having a viewing end. The system further comprising a battery operated unitary digital camera having an optical input, viewing screen, digital signal processor, memory with embedded software for processing data from the processor and for displaying an image on the viewing screen, and a coupler located at the distal end of the camera for removably connecting to the eyepiece of an endoscope.

In another embodiment, the distal end of the endoscope may include a charge coupled device or similar device for obtaining the image. The output of the CCD is coupled to the camera.

In accordance with the more specific aspects of the present invention, one embodiment includes a high speed data transfer component (IEEE 1394, USB and similar methods), which connects directly to the camera for sending signals from the camera to a personal computing device, removable data storage card and/or onboard mini hard-drive or flash memory and onboard controls, enabling more detailed camera control and image manipulation. Another embodiment of the present invention comprises a digital camera equipped with an LCD or similar screen for viewing the images, embedded software and one-touch controls for enhancing, manipulating and editing the images, and a media storage card for storing the images.

The invention described herein requires only a limited number of components, providing physicians with a portable, versatile, and less expensive system for endoscopic examinations and recording the images thereof. The system is easily transported to multiple locations, enabling healthcare providers greater versatility in the applications of endoscopic examinations and flexibility of the locations at which they examine patients. In addition to cost savings and flexibility, the high speed data transfer technology facilitates higher speed, lower cost data translation and manipulation, enhancing and expanding the quality of visual documentation generated without the need for special or costly computer systems.

BRIEF DESCRIPTION OF THE SEVERAL VIEWS OF THE DRAWINGS

A more complete understanding of the present invention may be had by reference to the following Detailed Description when taken in connection with the accompanying Drawings.

FIG. 2 is a perspective view of another embodiment of the present invention;

FIG. 3 is perspective view of yet another embodiment of the present invention;

FIGS. 10 and 11 are perspective views of a further embodiment wherein a camera and coupler are provided as a unitary component, including a swivel orientation adjuster;

DETAILED DESCRIPTION OF THE INVENTION

Figure 1:
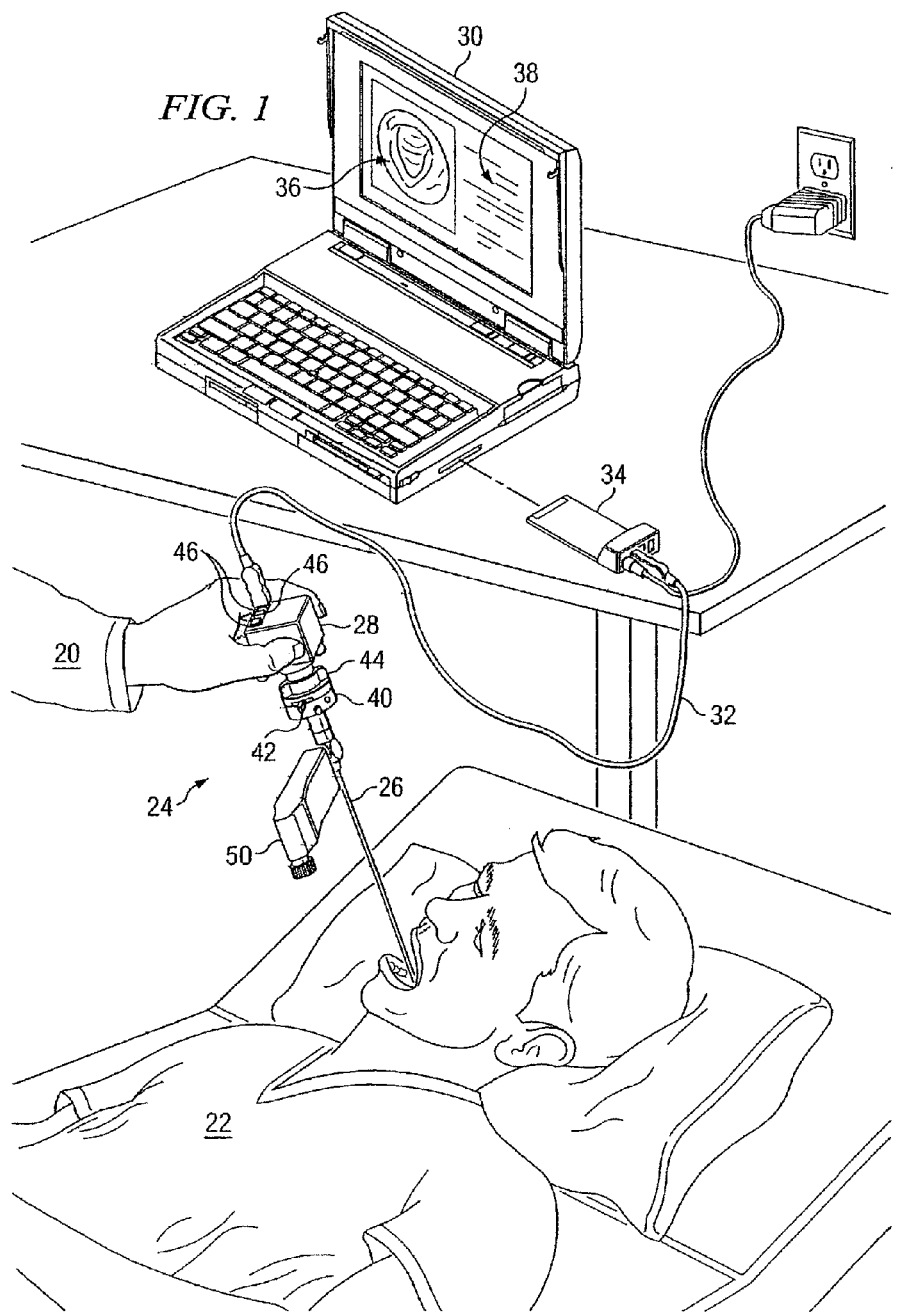
FIG. 1 is a perspective view illustrating one embodiment of the present invention in use.

Referring to the Drawings, and particularly to FIGS. 1 and 2 thereof, there is shown an endoscopic imaging system comprising a first embodiment of the invention. Referring specifically to FIG. 1, a physician 20 is shown performing an endoscopic examination of a patient 22 using an endoscopic imaging system 24. An endoscope 26 is inserted into the patient 22. The images seen by the endoscope 26 are received into a portable endoscopic digital camera 28 capable of high speed data transfer and then transmitted to a computer 30 by means of a high speed data transfer connection cable 32, for example a USB cable. The cable 32 connects into a multifunctional interface card 34, which also supplies power to the camera 28. Alternately, the high speed data transfer connection cable can connect directly to a computer or similar computing device without a multifunctional interface card if said high speed data transfer connection is built into the computing device. Examples of the high speed data transfer consistent with the present invention include various protocols such as IEEE 1394, USB, BLUETOOTH and 802ll.b (or similar wireless technology). As a further alternative, the camera 28 may be battery operated. The computer 30 enables the physician 20 to control the camera 28 and further manipulate the data received during the examination. The endoscopic images 36 are displayed on a computer screen 38. The computer screen 38 may either be an on-board screen on a notebook style computer, or an independent monitor networked with the computer 30, or a desktop workstation computer.

Referring specifically to FIG. 2, there is shown an enlarged view of the endoscopic imaging system 24 shown in FIG. 1. The endoscope 26 of FIG. 1 is constructed of a rigid material such as stainless steel, or other materials approved for use in medical applications. The endoscope 52 shown in FIG. 2 is constructed from a flexible material approved for use in medical applications. The endoscope 52 is coupled to a portable endoscopic digital camera 28 capable of high speed data transfer by a coupler 40. In one embodiment, the coupler 40 includes a standard C or C/S coupler and is equipped with a locking mechanism 42 which holds the endoscope 26 or 52 securely onto the camera 28. Alternately, there is no C or C/S coupler. The coupler 40 receives the images from the endoscope 52. The coupler 40 includes at least one lens assembly that moves to focus the image onto a transducer or other similar device internal to the camera 28. Additionally, the image coupler allows for zooming and magnification of the images. The coupler 40 couples to the camera 28 and a focus ring 44. The focus ring 44 assists the physician to focus the image to obtain a clearer, better quality image.

In one embodiment, the portable endoscopic digital camera 28 capable of high speed data transfer uses a single charged coupled device (CCD) (described further below) as the image acquisition device, together with a high speed data transfer input/output ports 46. Depending on the camera mode selected by the user at the computer 30, the portable endoscopic digital camera 28 transmits the images to the computer 30 where the images are viewed and stored. A digital camera, based on IEEE 1394 or the like, for use with the endoscopic imaging system 24 may also be equipped with a triple charged coupled device (CCD) and have multiple high speed data transfer input/output ports 46. The multiple high speed ports are beneficial because the additional throughput desired with the triple CCD. Additionally, the portable endoscopic digital camera capable of high speed data transfer may also be equipped with complimentary metal oxide semiconductors (CMOS) for image acquisition. The embodiment shown in FIGS. 1 and 2 include a light source 50 coupled to the endoscope 26, 52 and coupler 40. The light source 50 provides additional lighting for a better view of the area being examined by the endoscope 52. The light source 50 shown is battery operated. However, the light source may be operated by an external power source. Alternatively, an external light source and light guide cable may be provided as the light source. Still further, certain endoscopes are equipped with a light source.

Referring now to FIG. 3, there is shown an endoscopic imaging system 60 comprising a second embodiment of the invention. Many of the component parts of the endoscopic imaging system 60 are substantially identical in construction and function to component parts of the endoscopic imaging system 24 illustrated in FIGS. 1 and 2 and described hereinabove in conjunction therewith. Such identical component parts are designated in FIG. 3 with the same reference numerals utilized above in the description of the endoscopic imaging system 24, but are differentiated there from by means of a prime (') designation.

The endoscopic imaging system 60 differs from the endoscopic imaging system 24 of FIGS. 1 and 2 in that the endoscopic imaging system 60 includes a camera 28' with an on-board LCD screen 64 and on-board one-touch camera controls with embedded software for manipulating, enhancing, and adjusting the data. It will be appreciated that the screen may be an LCD screen, LED screen or any other similar monitor. Installed into the camera 28' is embedded memory in the form of a mini hard-drive or flash memory and/or a digital media storage card which stores the images from the endoscopic examination until the camera 28' can be downloaded into a personal computing device through the high speed connection cable 32'. Such memory is described further below.

Figure 4:
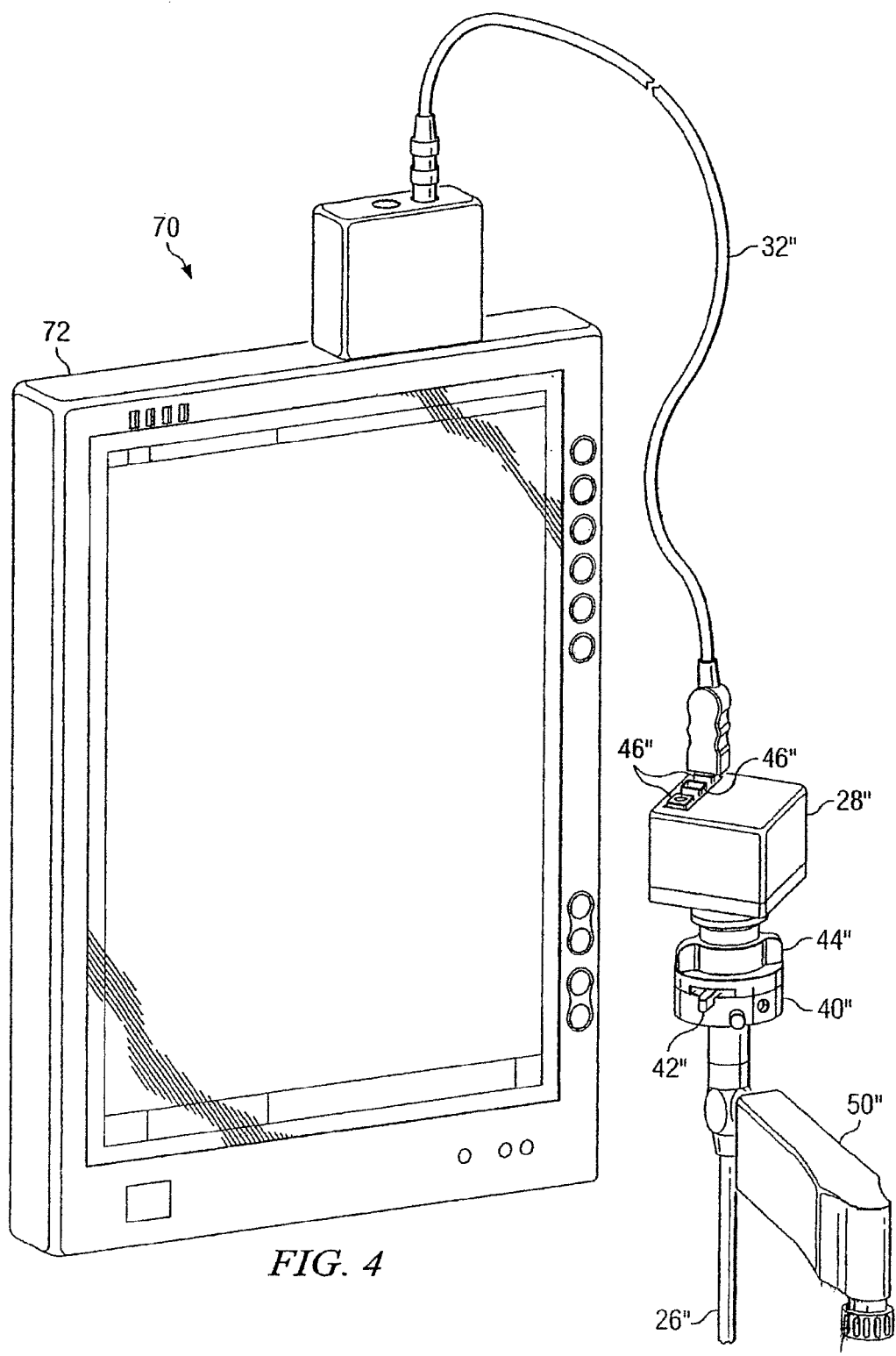
FIG. 4 is perspective view of yet another embodiment of the present invention.

Referring now to FIG. 4, there is shown an endoscopic imaging system 70 comprising another embodiment of the invention. Many of the component parts of the endoscopic imaging system 70 are substantially identical in construction and function to component parts of the endoscopic imaging system 24 illustrated in FIGS. 1 and 2 and described hereinabove in conjunction therewith. Such identical component parts are designated in FIG. 4 with the same reference numerals utilized above in the description of the endoscopic imaging system 24, but are differentiated there from by means of a prime (") designation.

The endoscopic imaging system 70 differs from the endoscopic imaging system 24 of FIGS. 1 and 2 in that the endoscopic imaging system 70 is equipped with a hand-held personal computing device 72. The hand-held personal computing device 72 may be an iPod® as manufactured by Apple Computer, Palm Pilot™, or other similar personal computing devices known to those skilled in the art.

Figure 5:
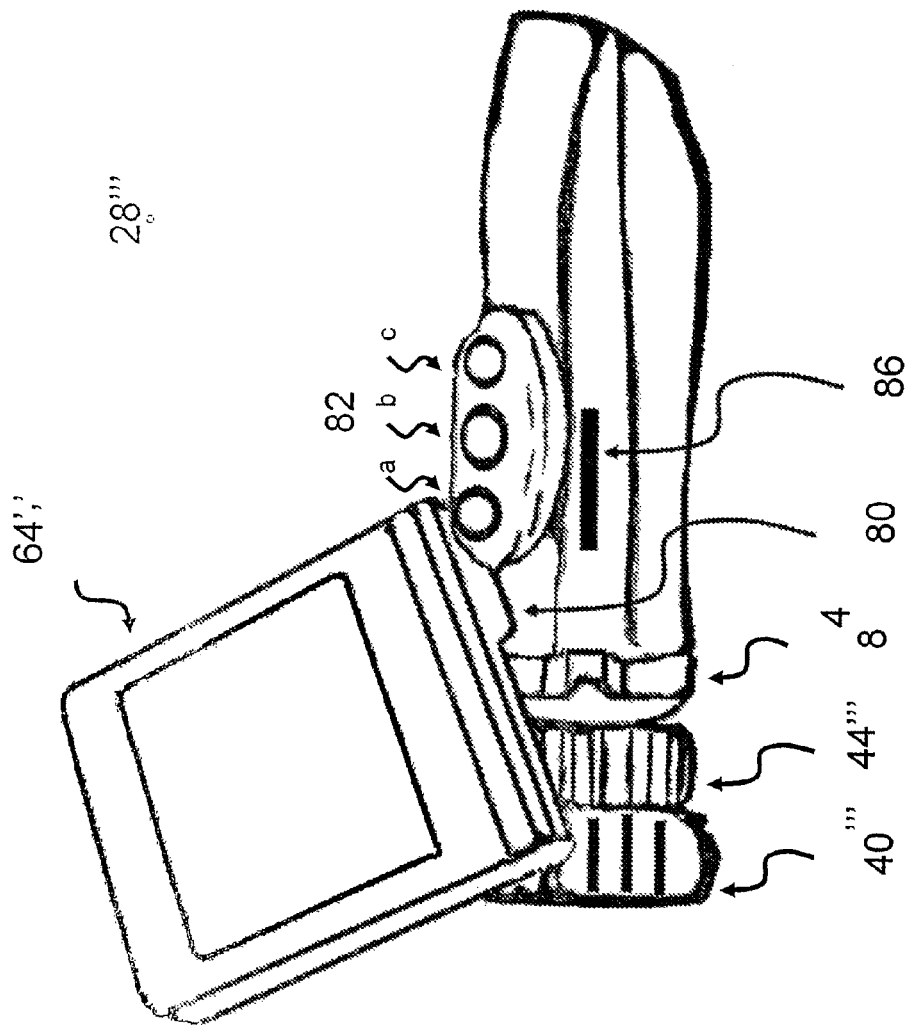
FIG. 5 is a perspective view of another embodiment wherein a camera and coupler are provided as a unitary component, and includes a viewing screen.

FIG. 5 is a perspective view of another embodiment wherein a camera 28''' and coupler 40''' are provided as a unitary component, including a viewing screen 64'''. The viewing screen may be a liquid crystal display (LCD) or thin film transistor (TFT) screen. The viewing screen is mounted to the unitary camera unit via a swivel pivot point hinge 80. The camera unit includes user input controls 82 (*a*,*b*,*c*) for manipulating, enhancing and adjusting data, via embedded software. The unitary camera unit also includes an endoscope coupler 40''' for coupling to an endoscope such as that shown in FIG. 1-4. In addition, the unitary camera unit includes a focus ring 44 and a zoom ring 84 so that the physician may adjust the image for display on the viewing screen. However, the function of focus and zoom may also be accomplished via the embedded software and the user input controls 82. A slot 86 is provided for connection of a removable flash memory card (see FIG. 15). The removable flash memory card allows the data to be transferred to another device in order to view or store the data, as desired.

Figure 6:
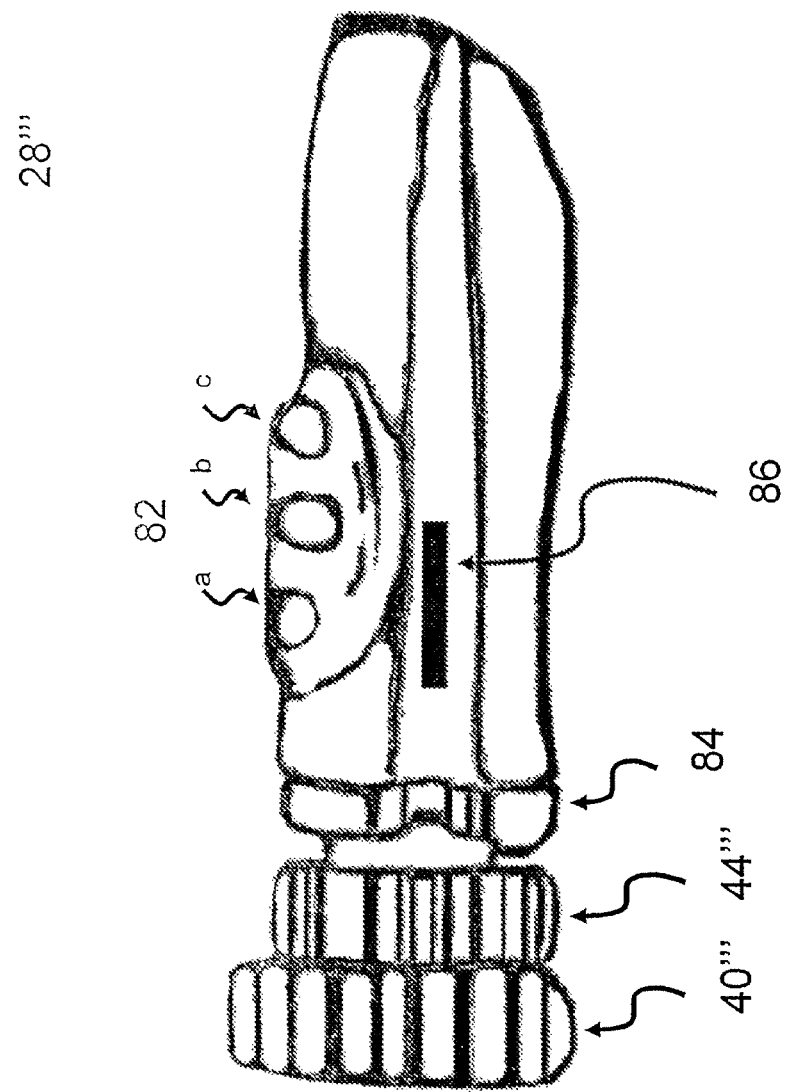
FIG. 6 is a perspective view of another embodiment wherein a camera and coupler are provided as a unitary component, and includes a high speed data transfer port.

FIG. 6 is a perspective view of another embodiment wherein a camera 28''' and coupler 40''' are provided as a unitary component, including a high speed data transfer port 46 (not seen in FIG. 6). The high speed data transfer port 46 allows connection to the various external devices as noted above, such as a handheld PC device.

Figure 7:
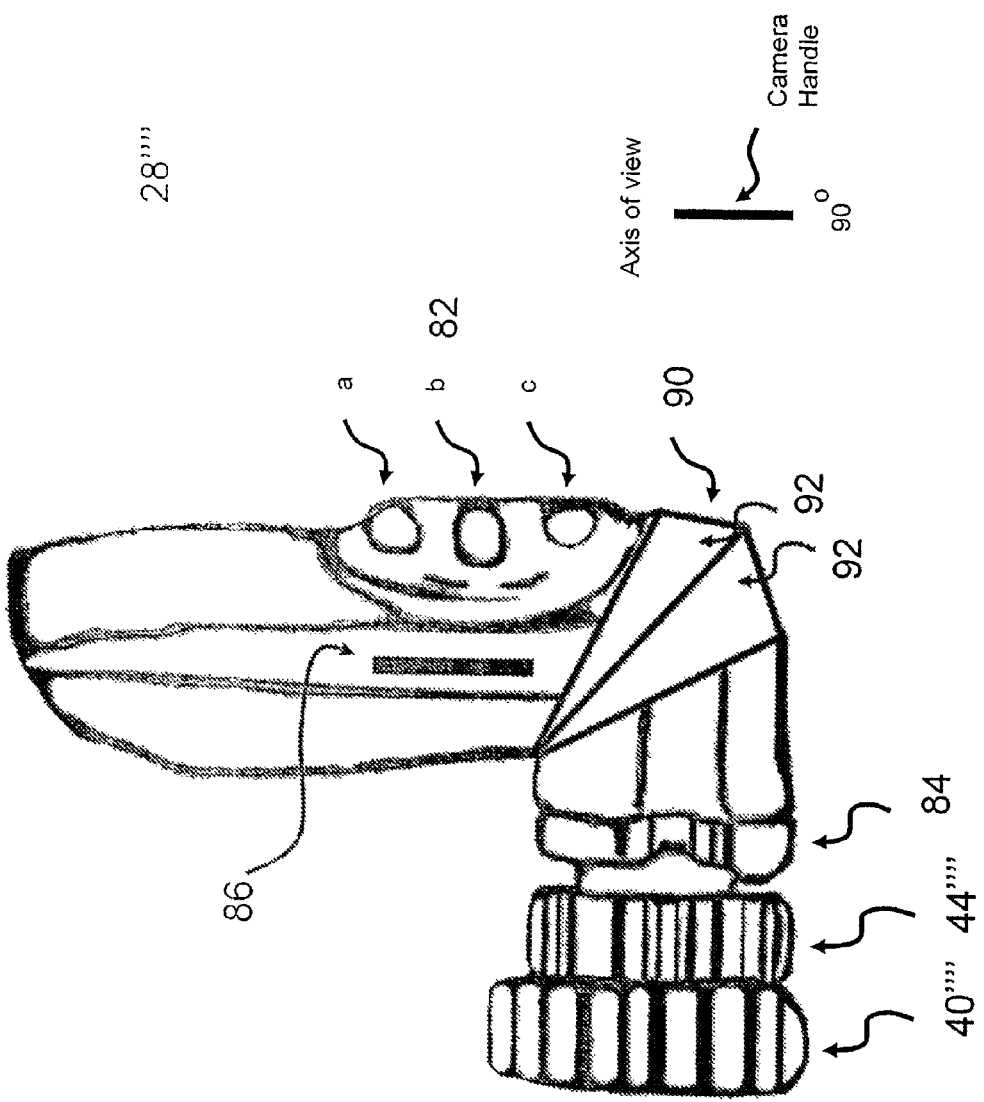
FIG. 7 is a perspective view of another embodiment wherein a camera and coupler are provided as a unitary component, and includes a swivel orientation adjuster.
Figure 8:
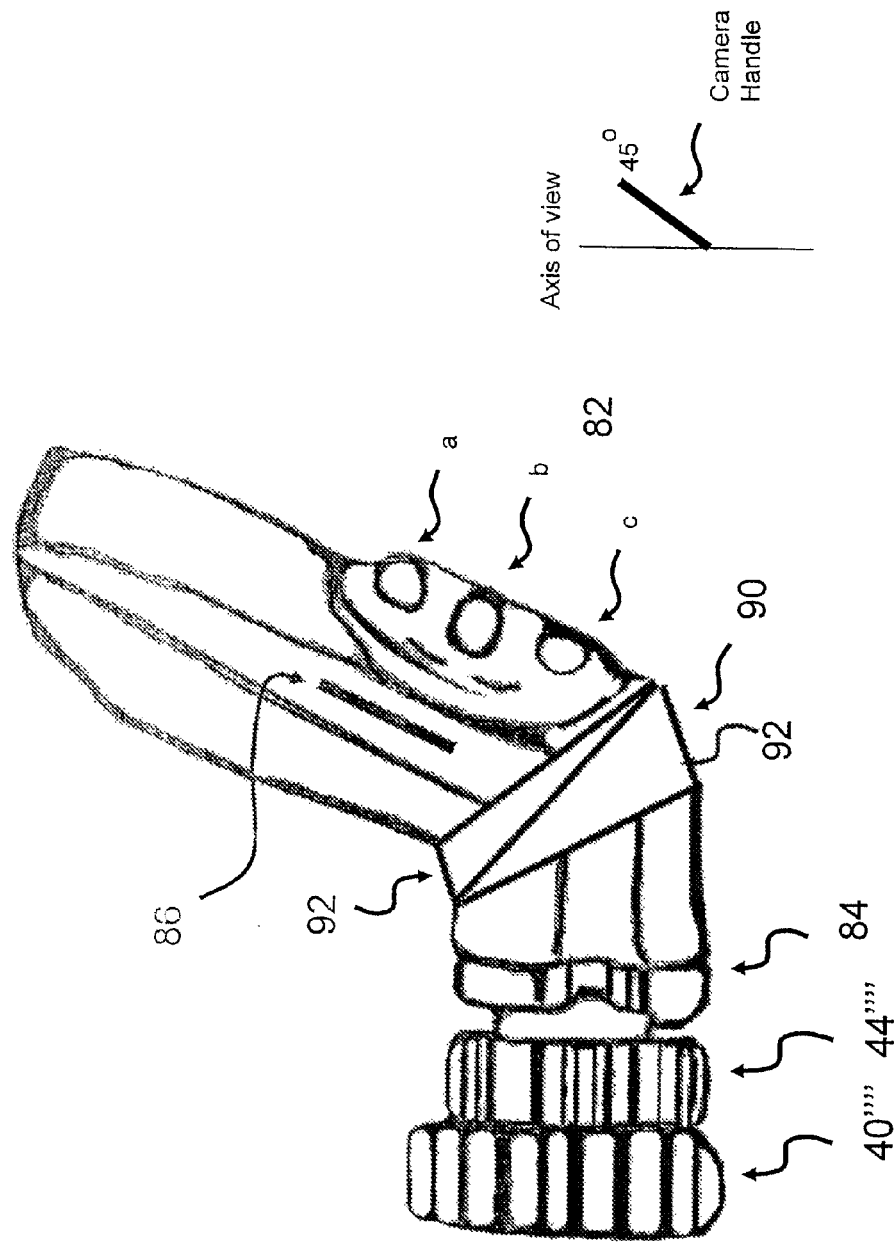
FIG. 8 shows the camera unit of FIG. 7 but with the camera unit adjusted to different orientation.

FIG. 7 is a perspective view of another embodiment wherein a camera 28'''' and coupler 40'''' are provided as a unitary component, including a swivel orientation adjuster or elbow joint 90. The swivel orientation adjuster 90, in one embodiment, is a series of one or more sleeves 92 having a certain profile such that twisting or rotating the camera unit allows the camera unit to assume various orientations, such as the one shown in FIG. 7 and in FIG. 8.

Figure 9:
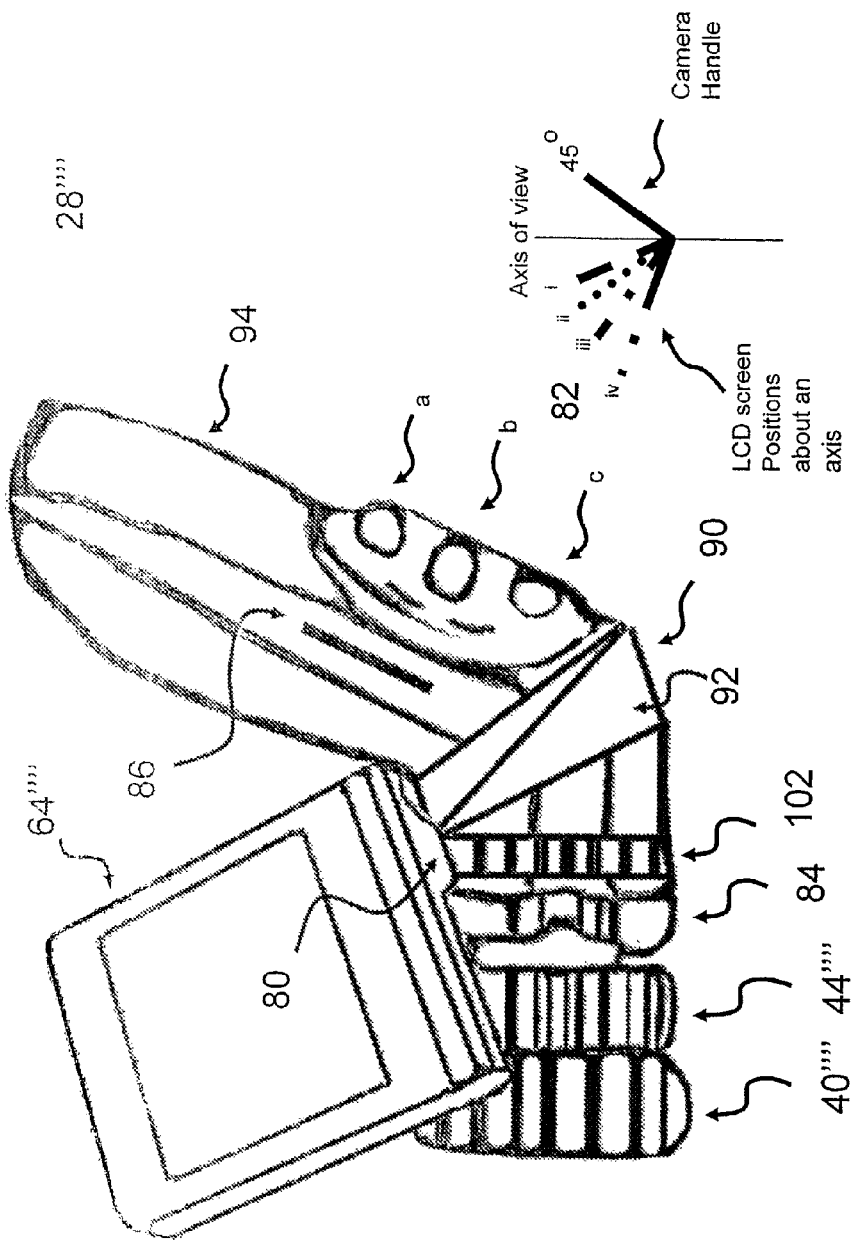
FIG. 9 is a perspective view of another embodiment wherein a camera and coupler are provided as a unitary component, including a movable viewing screen and a swivel orientation adjuster.

FIG. 9 is a perspective view of another embodiment wherein a camera 28'''' and coupler 40'''' are provided as a unitary component, including a hinged coupled flip viewing screen 64'''' and a swivel orientation adjuster 90. It will be appreciated from FIG. 9 that the handle or camera body 94 assumes one orientation with respect to the coupler portion 40'''' and the flip viewing screen 64'''' assumes another and independent orientation with respect to the coupler portion.

FIGS. 10 and 11 show a variation of the adjuster 90. In this instance, the camera body 94 is coupled to an extension portion 96 at a pivot point which includes a pin 98. The camera body 94 includes a plurality of recesses 99 which receive a detent or pawl 100 to lock the body 94 and extension portion 96 in position. FIG. 10 shows an in-line orientation, wherein FIG. 11 shows an offset orientation of 90 degrees.

Figure 12:
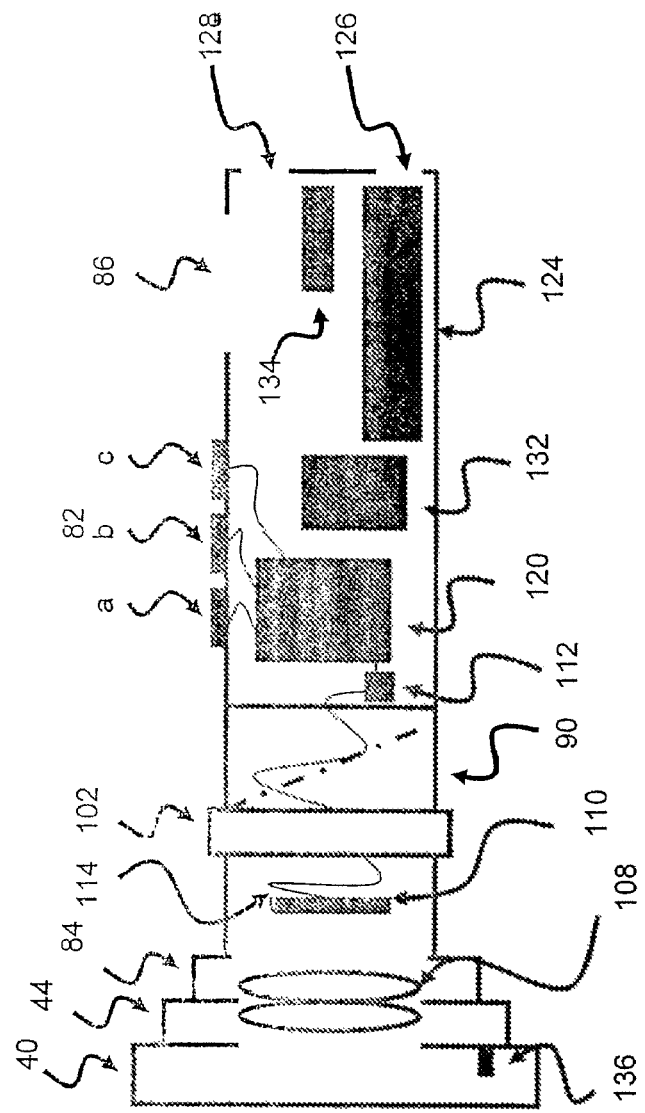
FIG. 12 is a schematic of one embodiment of the unitary component.
Figure 13:
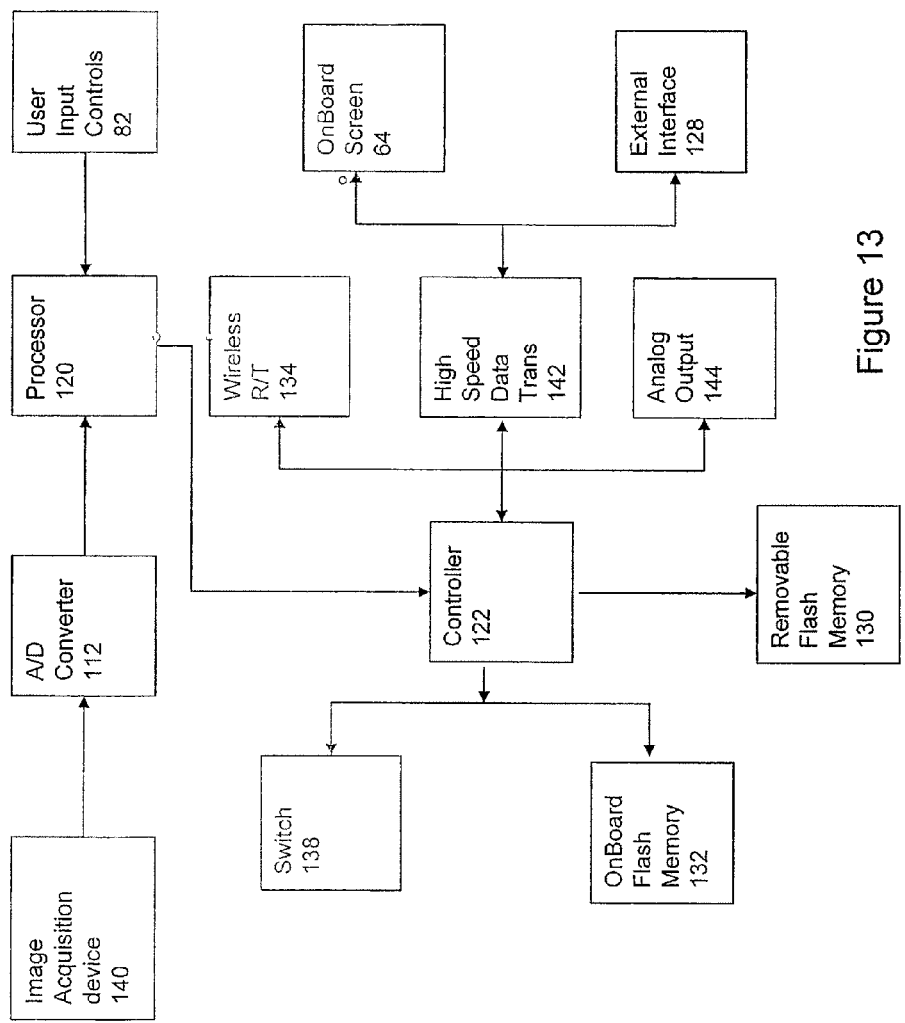
FIG. 13 is a functional block diagram of one embodiment of the present invention.

FIG. 12 is a schematic of one embodiment of the unitary component. The endoscope coupler 40 is shown adjacent to the focus ring 44 which is adjacent to the zoom ring 84. The zoom ring 84 is adjacent to the image ring 102. The elbow joint 90 is shown connected to the body 94. The distal end of the body 94 of the camera unit contains the optical lens mechanism 108 which accommodates the focus and zoom functions, in order to direct the image onto the CCD or CMOS chip 110. The chip 110 is connected to the input of an analog-to-digital converter 112 via the ribbon wire 114. The output of the A/D converter 112 is coupled to a digital signal processor/camera processor 120. The user input controls 82 are coupled to the processor 120, or alternatively to a controller 122 such as shown in FIG. 13. The proximal end of the body 94 also includes a battery 124 and a connector 126 for external DC. The proximal end of the body 94 also includes an I/O high speed data transfer port 128 and a connector 86 for a removable flash memory card 130 (see FIG. 13). The body 94 also includes on board flash memory 132. Finally, a wireless radio transceiver 134 is shown for wireless downloading of data and wireless control of the camera unit. A power on peg 136 is shown. The power on peg 136 includes a switch 138 (see FIG. 13) which is coupled to the controller 122. The memory 132 includes a code for a sleep mode and power up routine, or similar battery saving features. The unit is normally in a sleep mode as one skilled in the art will appreciate. Upon the coupler 40 engaging an endoscope, the power on peg 136 is engaged and the power up routine is initiated. As is shown, ribbon wire 114 or other conductors extend within the elbow joint 90 from the distal coupler end to proximal body.

FIG. 13 is a functional block diagram of one embodiment of the present invention. The image acquisition device 140 may be an CCD chip 110, for example. The high speed data transfer port 142 is shown coupled to the on board screen 64 and the port 128 for connection to an external device. An analog output 144, such as audio S, is provided for coupling to an external device.

Figure 14:
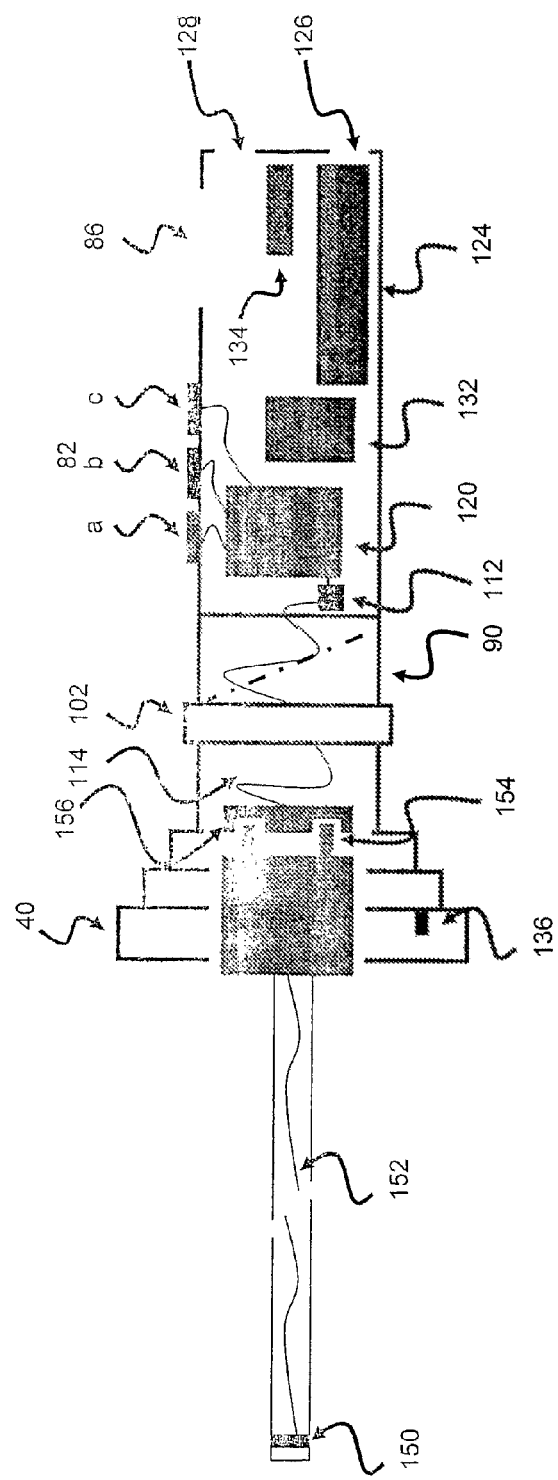
FIG. 14 is a schematic of one embodiment of the present invention with the charge coupled device at the distal end of the endoscope.

FIG. 14 is a functional block diagram of one embodiment of the present invention with the charge coupled device 150 or other image acquisition device at the distal end of the endoscope. Conductors 152 are coupled to the device 150 and extend within the endoscope. The coupler 40 includes an electrical and mechanical connector 154 for coupling to an electrical and mechanical connector 156 having the ribbon connector wire 114. The electrical and mechanical connector 154 is also adapted for coupling to the endoscope and the conductors 152. For example, the connector 154 may include a portion connected to the endoscope and a portion connected to the coupler 40. The system of FIG. 14 is otherwise similar to that shown in FIG. 12.

Another embodiment of the present endoscopic camera 28 is shown in FIGS. 15 through 28 as comprising camera housing 200, display housing 210 enclosing viewing screen or video display 64, coupler 40, focus ring 44, and zoom ring 84. Both camera housing 200 and display housing 210 are preferably constructed from high impact plastic, although other sturdy materials may alternatively be used. Camera housing 200 includes an elongated main body region 201, a bulbous gripping region 202, and two elongated, indented forefinger or index finger accepting regions 203 on opposing left and right sides of main body region 201, proximate bulbous gripping region 202. A high speed I/O data transfer port 128 permits both digital data transfers to an external computer, such as a personal desktop or laptop computer, via a conventional Universal Serial Bus (USB) interface, as well as analog video output to a conventional video display monitor, via an appropriate accessory AV cable. Data transfer port 128, when coupled to a PICTBRIDGE®-compatible USB printer, permits still images captured by the present endoscopic camera to be printed directly, without the need for an intermediate external computer. A power-on switch (not shown) is disposed on the left side of main body region 201.

A snap fit battery door 206, removable with the aid of a plurality of gripping ribs 207, permit access to a portion of the interior of camera housing 200, to permit removal and replacement of a rechargeable battery powering the endoscopic camera, as well as the insertion and removal of a flash memory card storing captured motion video and/or still images. A plurality of screw holes 205 and associated screws 204 permit camera housing 200 to be constructed from a plurality of housing portions.

Figure 17:
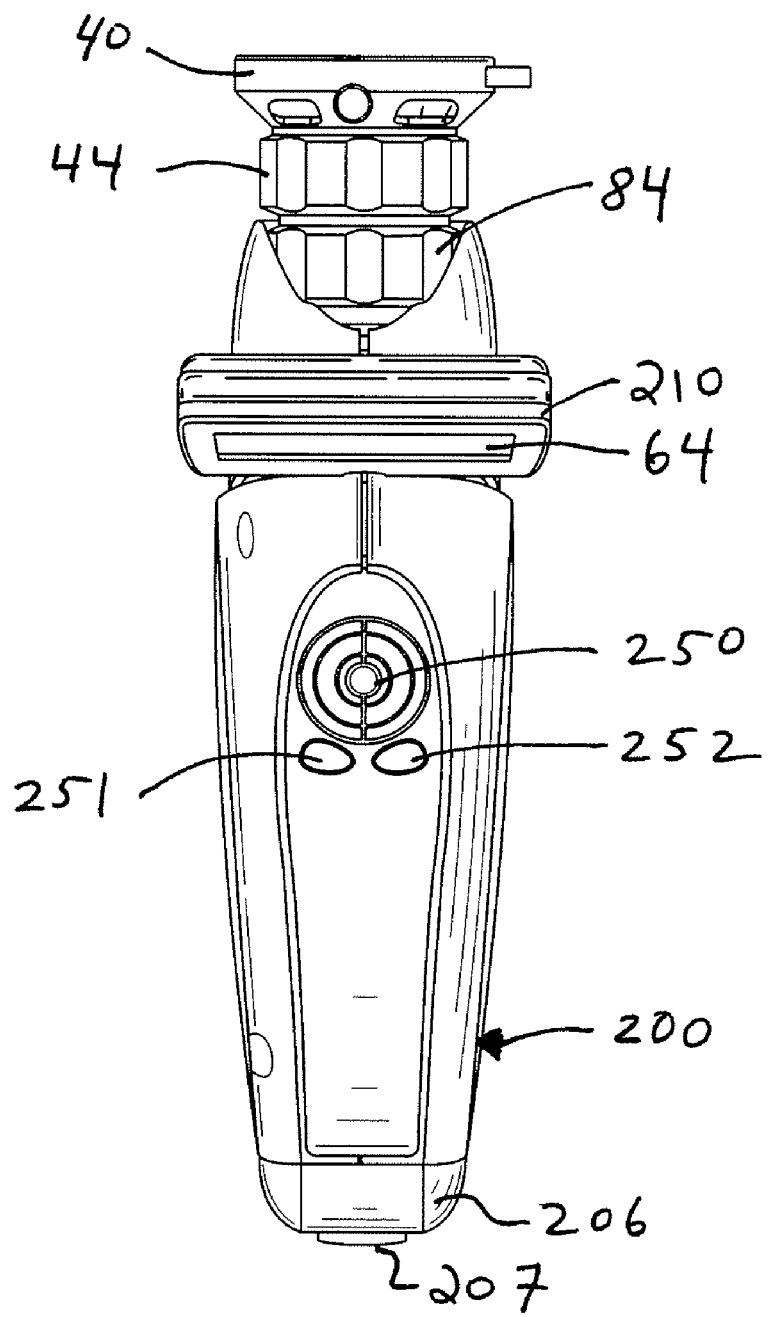
FIG. 17 is a top plan view of the embodiment of FIG. 15.
Figure 18:
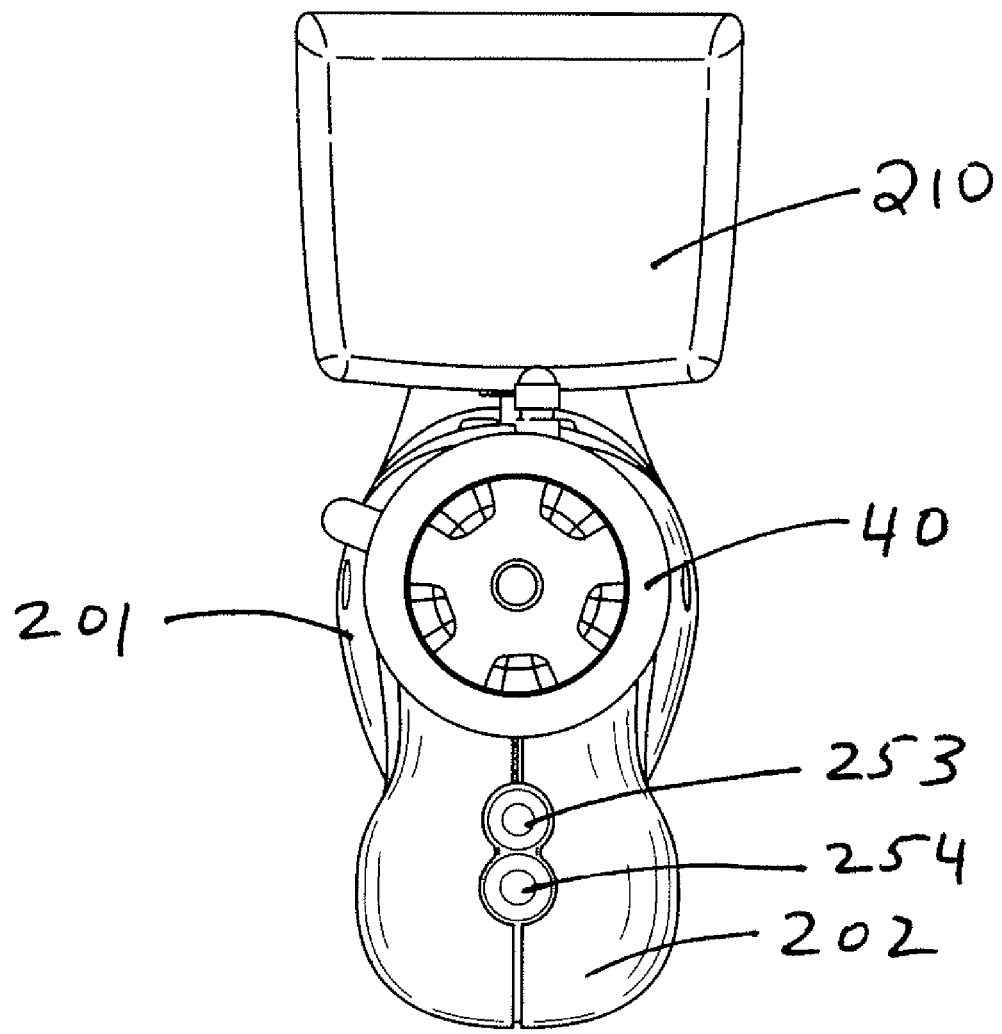
FIG. 18 is an elevated, front view of the embodiment of FIG. 15.
Figure 19:
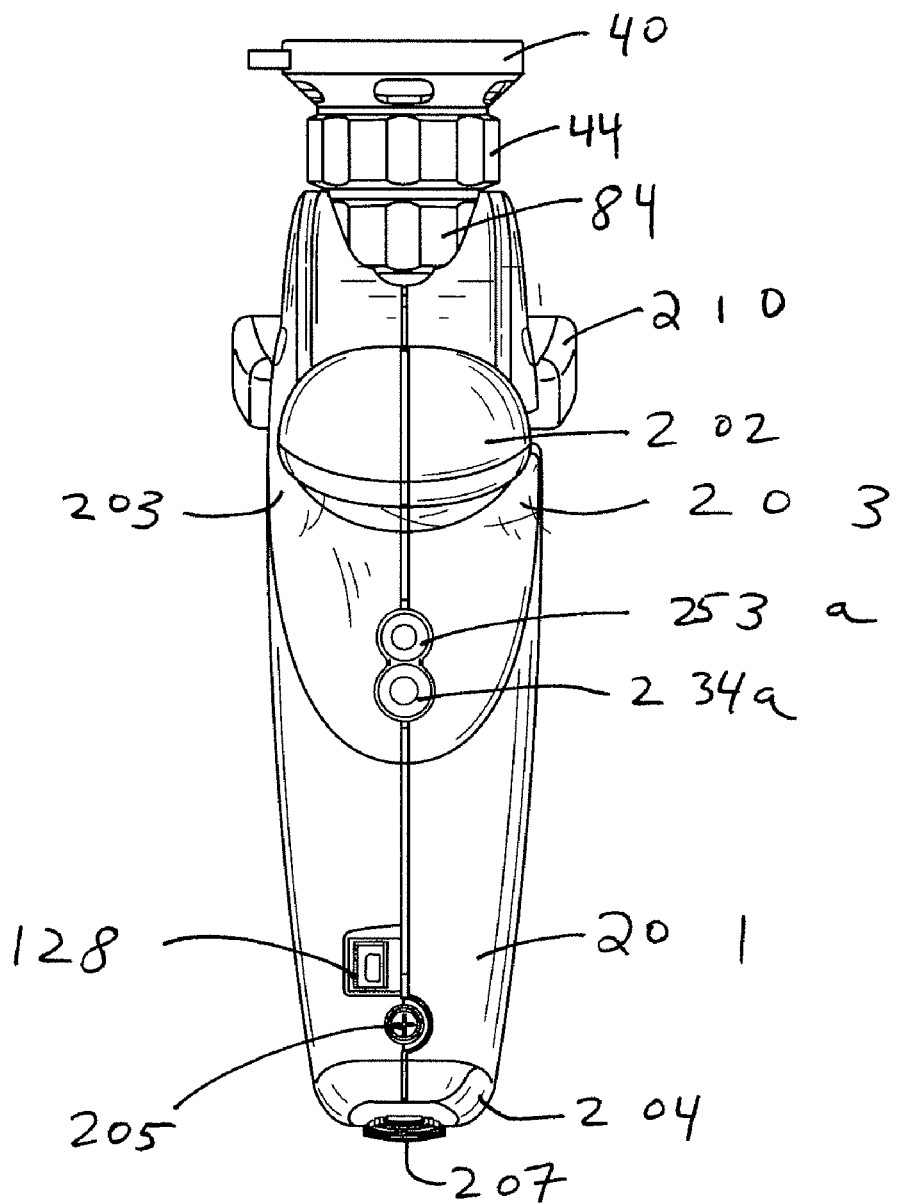
FIG. 19 is a bottom view of the embodiment of FIG. 15.

As best seen in FIGS. 17-19, a plurality of user input control switches are disposed on camera housing 200. In particular, the top surface of camera housing includes direction button 250, mode button 251, and menu button 252. Direction button 250 is preferably a digital joystick, normally spring biased to remain in a central, vertical orientation, which may be momentarily rocked into forward, reverse, left and right orientations, relative to its central orientation. One of the functions of direction button 250 is to select a digital zoom level for image viewing and capture. Movement of direction button to the forward or reverse orientation causes an associated positive or negative change in the digital zoom level of the image to be viewed and the still or motion video image to be captured. In a preferred embodiment, a zoom level of up to 4× digital magnification may be selected using direction button 250. Mode button 251 and menu button 252 are preferably pushbutton, momentary switches.

Direction button 250 performs several additional functions, in conjunction with mode button 251, menu button 252, and an on-screen menu presented to the physician using video display 64, under control of the microprocessor, or digital signal processor, contained within the housing of the present endoscopic camera. In particular, using these three buttons, the physician can play back video clips and select from amongst still images for viewing, view an index of "thumbnail" images of such recordings and still images, fast forward, fast reverse, and stop playing video clips, select a video/still capture image resolution mode of 1, 3 or 6 mega-pixels, record audio voice clips, turn image date stamping on and off, enable and disable automatic image stabilization, adjust the white balance setting of captured images, turn image histogram displays on and off, choose from amongst natural color, black and white, and sepia toned image capture, manually adjust the image exposure level, activate a 10-second electronic shutter self-timer, enable/disable on screen display icons, select the video output resolution (i.e., 640×480 or 320×240 pixels), and combine two images taken individually into one photograph.

Moreover, the on-screen menu may also be employed to delete images and video clips, view a "slide show" of previously captured images, and to print images directly to an attached, PICTBRIDGE®-compatible printer. In addition, the on-screen menu may be used to set an internal date and time, enable/disable audio beep sounds, set the display flicker frequency to 50 Hz or 60 Hz, set the direct, analog TV output of the high speed I/O data port to either NTSC or PAL video formats, set the brightness of video display 64, format the internal and removable storage media; turn automatic shutoff on and off, set the language for the on screen display, and set a mode of operation of the USB port (depending upon the setting, when connected to a personal computer via the high speed USB port, the on screen display will either display a menu permitting the physician to select a desired connection mode, will automatically connect in "removable disk" mode, or will automatically enter printer mode).

In addition to direction button 250, mode button 251, and menu button 250, as best seen in FIGS. 18 and 19, the present endoscopic camera further includes two redundant motion video record buttons 253, 253a; and two redundant still photograph shutter buttons 254, 254a, all comprising momentary, pushbutton switches and disposed on camera housing 200. In particular, either video record button 253 or 253a may be depressed to record a video clip, and either still photograph shutter button 254 or 254a may be depressed to capture a still photograph. As shown in FIG. 18, a first grouping of video record and still photograph shutter buttons, video record button 253 and still photograph shutter button 254, are disposed on a front surface of bulbous gripping region 202. As shown in FIG. 19, a second grouping of video record and still photograph shutter buttons, video record button 253a and still photograph shutter button 254a, are disposed on a bottom surface of elongated main body region 201, behind bulbous gripping region 202.

The provision of redundant video record and still photograph shutter buttons serve to facilitate ease of operation by the physician in recording video clips and still images using the present endoscopic camera. In particular, depending upon the type of endoscope attached to the present endoscopic camera, as well as the type of endoscopic inspection being performed, it may be convenient for the physician to hold the present endoscopic camera in a variety of different manners. Depending upon the physician's particular orientation and grip of the present endoscopic camera and attached endoscope, it may be more convenient in some circumstances to use buttons 253 and/or 254; and in other instances to instead use buttons 253a and/or 254a.

Figure 26:
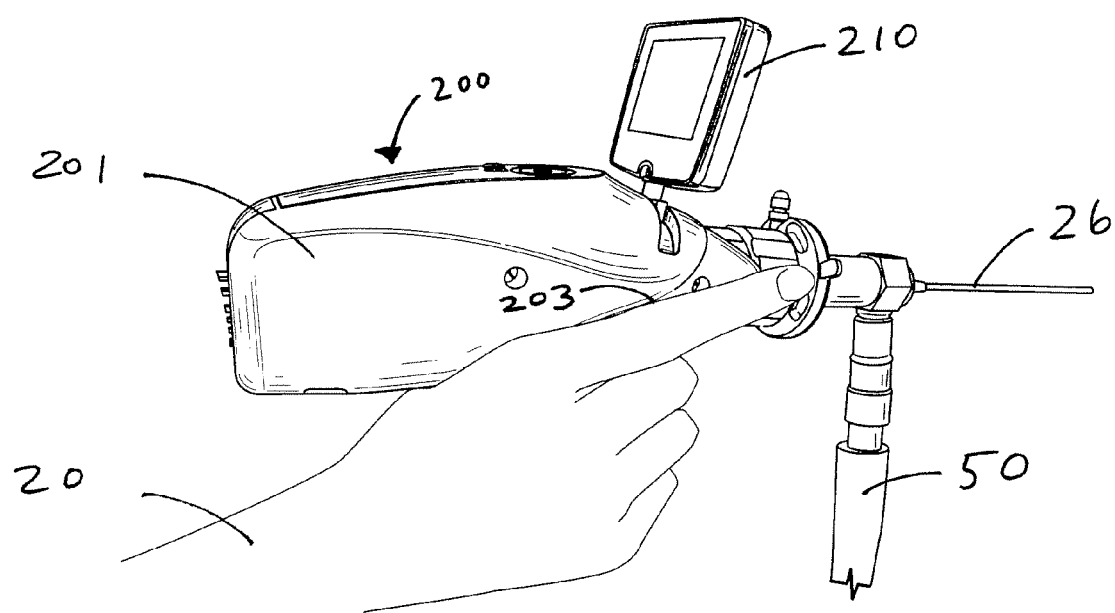
FIG. 26 is a perspective view of the embodiment of FIG. 15 showing, in particular, the camera connected to an external light source and a rigid endoscope, and being held in a pistol grip manner.
Figure 27:
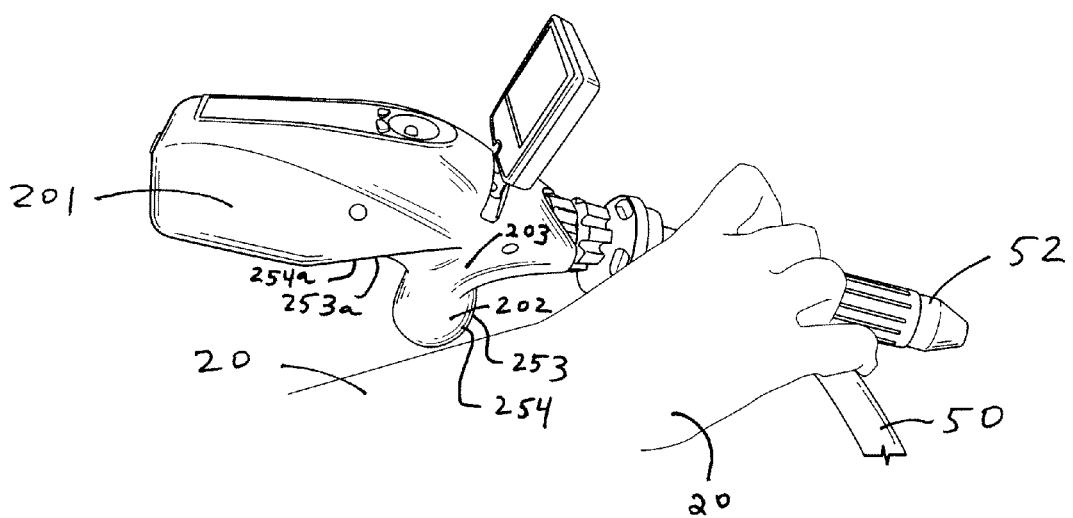
FIG. 27 is a perspective view of the embodiment of FIG. 15 showing, in particular, the camera connected to an external light source and a flexible endoscope, and being held in a top, distal tip control manner.
Figure 28:
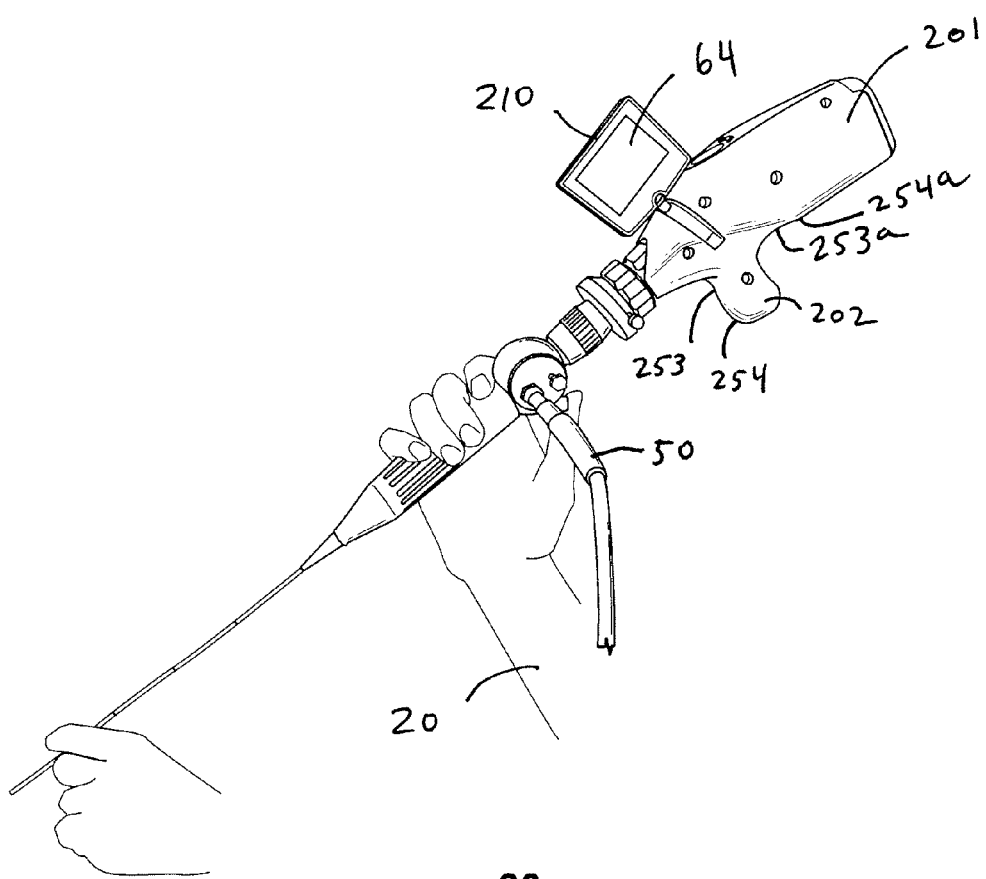
FIG. 28 is a perspective view of the embodiment of FIG. 15 showing, in particular, the camera connected to an external light source and a rigid endoscope, and being held in a bottom, distal tip control manner.

Several different ways in which the present endoscopic camera and an attached endoscope may be held by the physician are shown in FIGS. 26-28. In FIG. 26, the physician 20 is shown holding camera housing 200 in a right-handed, pistol grip fashion whilst performing otolaryngology using a rigid endoscope 26 and an external light source 50. As shown in FIG. 26, the physician's middle, ring and little fingers of the right hand are all wrapped around the bulbous gripping region of the camera housing. This bulbous gripping region may be substantially bulbous or bulb-like, substantially spherical, substantially spheroidal, substantially oblate spheroidal, or substantially ellipsoid in shape. The physician's forefinger, or index finger, is placed along elongated indented forefinger accepting region 203 on the right-hand side of camera body 201. When held in this manner, it will be more convenient for the physician to record video clips and still images using video record button 253 and still photograph shutter button 254, respectively, by using the middle or ring finger to depress the desired button in a trigger-like manner. Accordingly, as best seen in FIG. 26, housing 200, including the combination of bulbous gripping region 202 (obscured by the physician's hand in this figure), forefinger accepting region 203, and buttons 253 and 254, provide a highly ergonomic means of holding the present endoscopic camera. Moreover, inasmuch as two, substantially identical forefinger accepting regions 203 are symmetrically disposed on opposing sides of camera housing 200, and inasmuch as buttons 253 and 254 are disposed proximate a front, central region of bulbous gripping region 202, the present endoscopic camera may be held and operated in a pistol grip manner using either the left hand or the right hand.

Another manner of gripping the present endoscopic camera, in conjunction with an attached flexible endoscope 52, is shown in FIG. 27. As shown, the physician 20 is holding the flexible endoscope in a top, distal tip control manner. When so held, the physician has relatively easy access to either buttons 253 and 254, or buttons 253a and 254a, and can use whichever is considered by the physician to be most convenient.

Yet another manner of gripping the present endoscopic camera, in conjunction with the use of a flexible endoscope, is shown in FIG. 28. As shown, the physician 20 is holding the flexible endoscope in a bottom, distal tip control manner. Again, the he physician has relatively easy access to either buttons 253 and 254, or buttons 253a and 254a, and can use whichever is considered to be most convenient.

Still another manner of gripping the present endoscopic camera, not shown in the drawings, is for the physician to "palm" the elongated main body region with an overhand grip. When so held, it is generally more convenient for the physician to depress, or squeeze, buttons 253a and/or 254a, on the underside of the camera housing, to record a video clip or take a still photograph, respectively.

Figure 20:
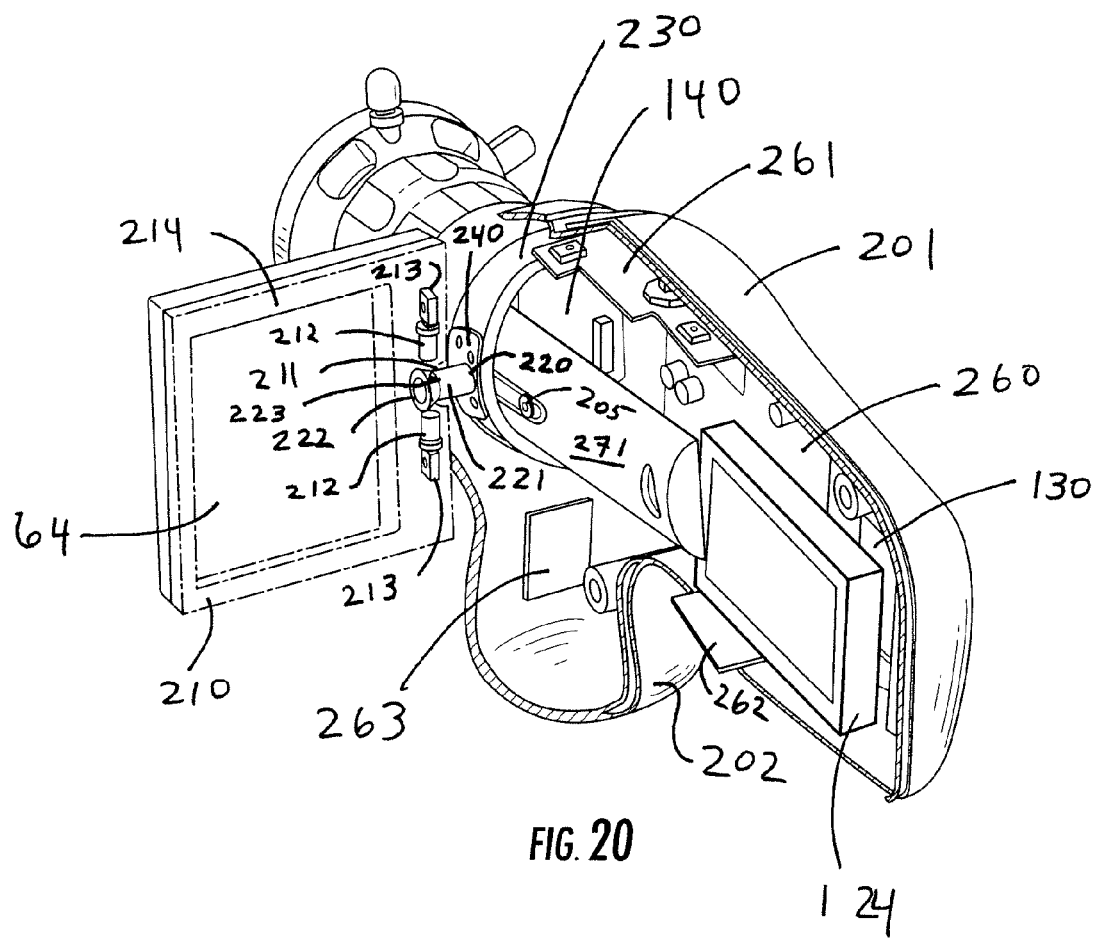
FIG. 20 is a perspective view of the embodiment of FIG. 15, partially in section.
Figure 21:
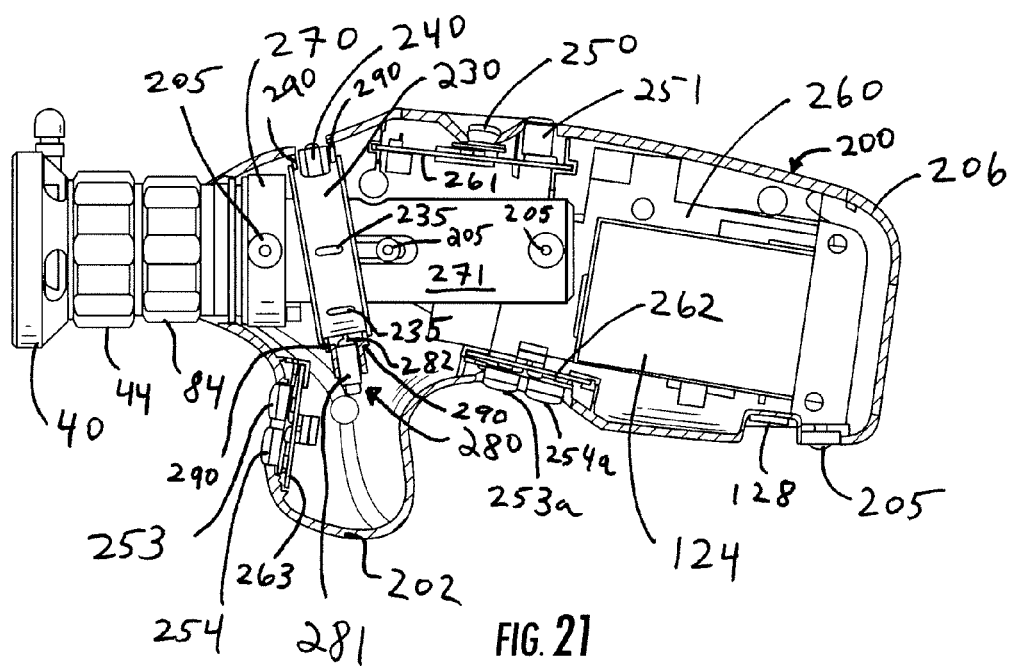
FIG. 21 is an elevated, left side view of the embodiment of FIG. 15, partially in section, with the display portion omitted for clarity.

As best seen in FIGS. 20 and 21, display housing 210 and, in turn, video display 64, are coupled to main camera body 201 via display swivel post 220, display rotational connector 230, and display post connector 240. Display swivel post 220 comprises stem portion 221, swivel head portion 222, central bore 223, and a longitudinal axis extending through central bore 223. Swivel head portion 222 is retained within an interior region of display housing 210 by swivel hinge pins 212 which, in turn, are maintained in position by respective associated retention nuts 213. Stem portion 221 of display swivel post 220 extends from bottom aperture 211 of display housing 210 and into camera body 201 at display rotating slot 208 (as shown, for example, in FIG. 16). Electrical conductors, such as a ribbon cable, are passed through central bore 233 to electrically connect video display 64 to a printed circuit board carried within camera housing 200.

Figure 22:
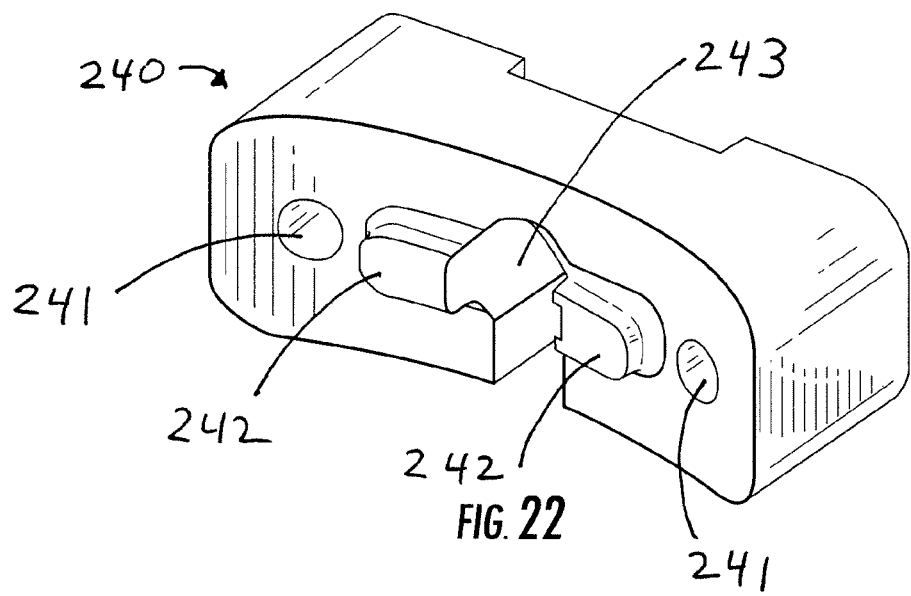
FIG. 22 is an enlarged, bottom perspective view of the display post connector of the embodiment of FIG. 15.
Figure 23:
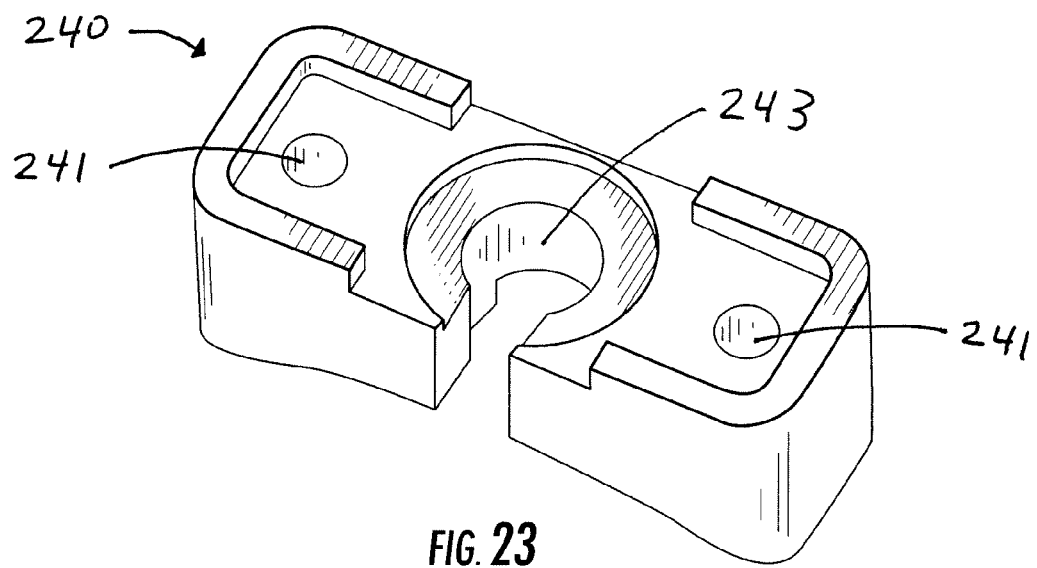
FIG. 23 is an enlarged, top perspective view of the display post connector of the embodiment of FIG. 15.
Figure 24:
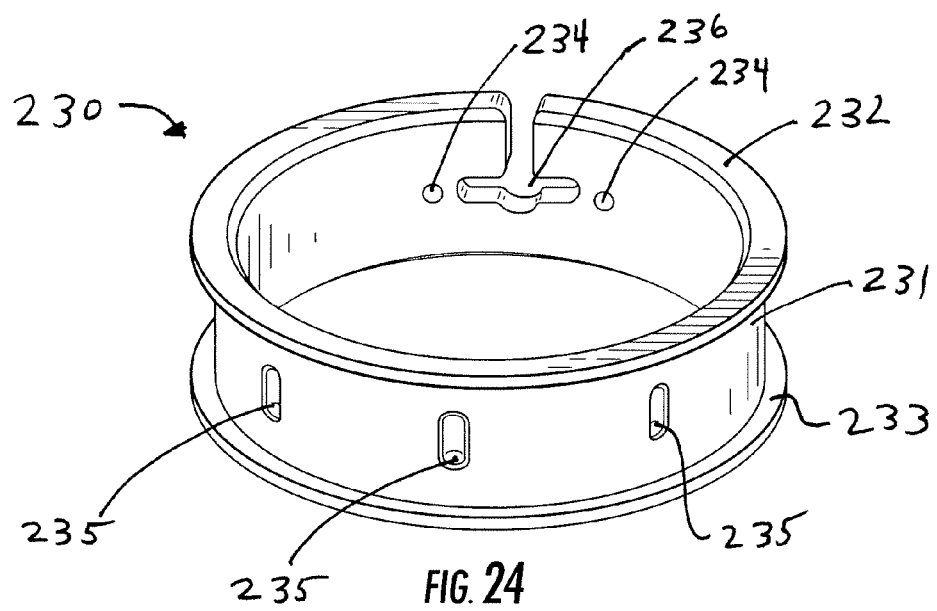
FIG. 24 is an enlarged, bottom perspective view of the display rotational connector of the embodiment of FIG. 15.
Figure 25:
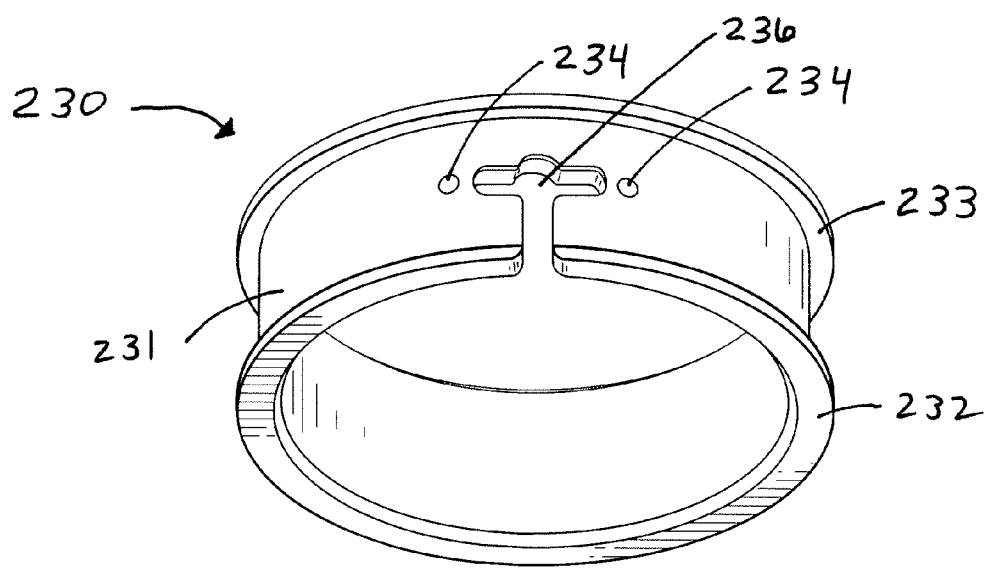
FIG. 25 is an enlarged, top perspective view of the display rotational connector of the embodiment of FIG. 15.

As shown in FIGS. 22-23, display post connector 240 includes two mounting apertures 241, locking members 242, and display swivel post stem accepting aperture 243. As shown in FIGS. 24-25, display rotational connector 230 comprises annular ring 231, first flanged end 232, second flanged end 233, display post connector mounting apertures 234, a plurality of detent apertures 235, and display swivel post stem aperture 235. Display post connector 240 secures stem portion 221 of display swivel post 220 to display rotational connector 230, with a distal end of stem portion 221 extending through swivel post stem aperture 235. Upon attachment of display post connector 240 and, in turn, display swivel post 220 to display rotational connector 230, locking members 242 are disposed within aperture 236, and respective mounting apertures 241 and 234 are aligned and secured together with suitable fasteners.

Figure 15:
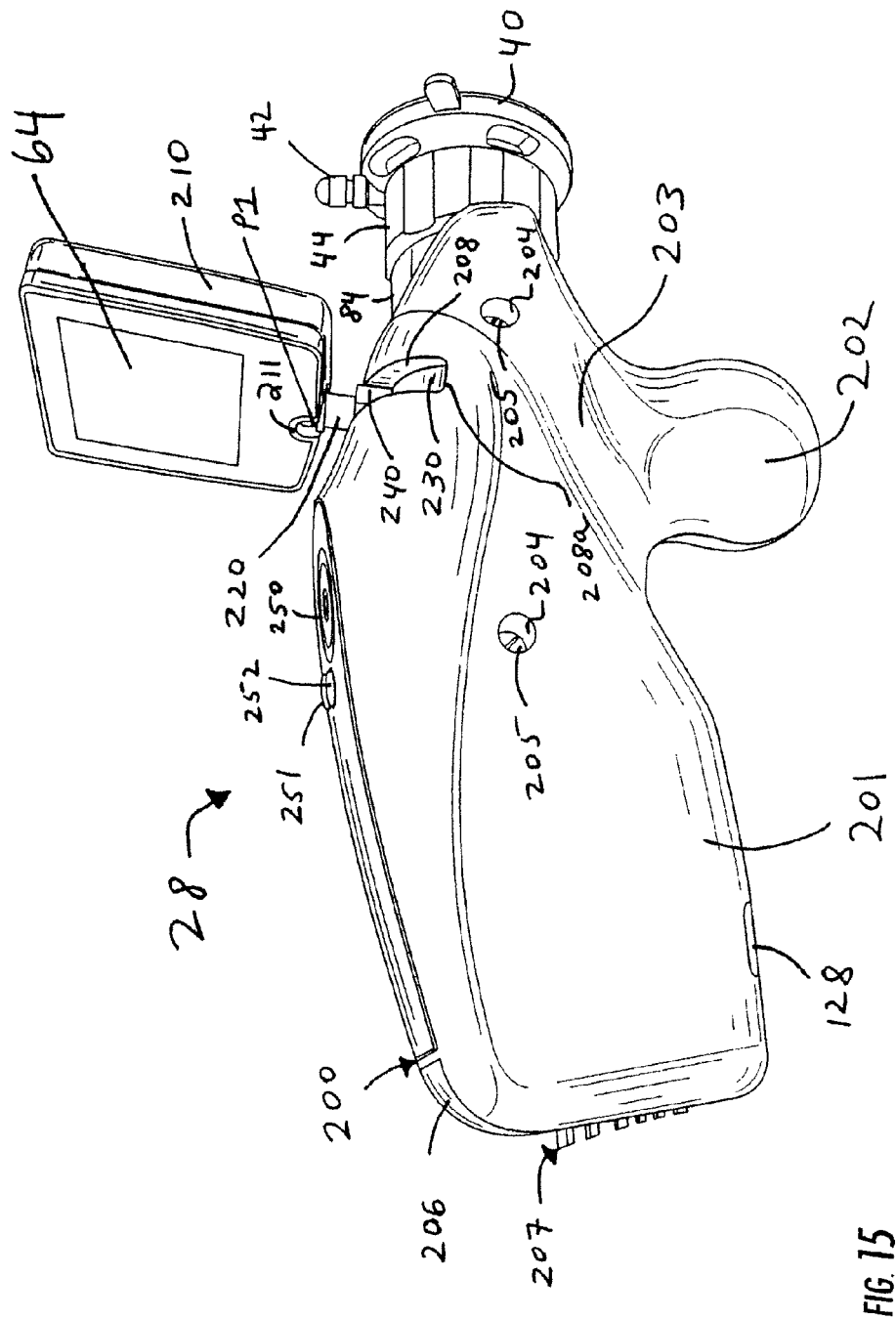
FIG. 15 is a perspective view of yet another embodiment of the present invention.
Figure 16:
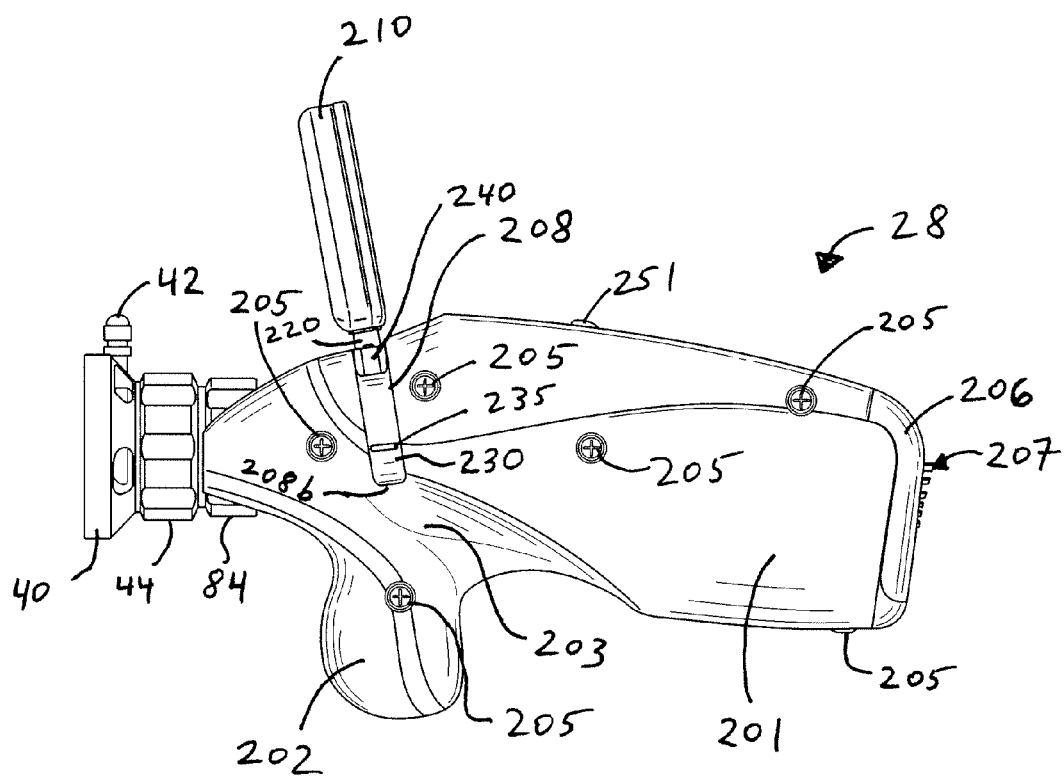
FIG. 16 is an elevated, left side view of the embodiment of FIG. 15.

Upon attachment of display post connector 240 and display swivel post 220 to display rotational connector 230, stem portion 221 of the display swivel post extends outwardly from camera housing 200, through display rotating slot 208. As the display rotational connector is rotated back and forth, stem portion 221 travels back and forth through slot 208, through a range of motion limited by contact of stem portion 221 with slot endpoints 208a and 208b, disposed on the right and left hand sides of main body region 201, respectively, as shown in FIGS. 15 and 16. Moreover, and as shown in FIGS. 15 and 16, slot 208 extends farther down the left hand side of main body region 201, to endpoint 208b, than down the right hand side of main body region 201, to endpoint 208a. This permits the display housing to be secured for overall storage of the present endoscopic camera by first rotating the display counter-clockwise fully to the left (as viewed from the rear of camera housing 200), until stem portion 211 contacts endpoint 208b, and then rotating the display housing back towards battery door 206, until the display rests substantially flat against the left hand side of elongated main body region 201.

As shown in FIG. 20, display housing bottom aperture 211 includes an arcuate portion disposed through top face 214 of display housing 210. This, in turn, permits display housing 210 and display 64 not only to be rotated about the longitudinal axis of display swivel post 220 (as the two swivel hinge posts rotate about display swivel post 220 proximate the juncture of stem portion 221 and swivel head portion 222) but further permits display housing 210 and display 64 to be simultaneously pivoted towards and away from camera body 201, as stem portion 221 enters and exits the arcuate portion of bottom aperture 211, respectively. In a preferred embodiment, the range of pivotal movement of display housing 210, relative to camera body 201, extends from a first position, wherein display housing 210 is substantially perpendicular to a longitudinal axis of camera housing 200 (extending through the camera housing main body region 201, the center of zoom ring 84, and the center of focus ring 44), to a second position, where display housing 210 rests substantially flat against camera housing main body region 201.

As best seen in FIG. 21, display rotational connector 230 is rotatably carried within camera housing 200, with annular ring 231 substantially concentric to the longitudinal axis of camera housing 200. A plurality of webs, or bosses 290, integrally formed with and extending inwardly from the inner surface of camera housing 200, cooperate with first flanged end 232 and second flanged end 233 of display rotational connector 230, permitting annular ring to 231 to rotate about the longitudinal axis of the camera housing while retaining connector 230 in position within the housing.

As shown in FIG. 21, a click stop member 280, disposed within camera housing 200, includes a click stop member housing 281, and a spring biased pin 282, biased by a spring member in an extended orientation, relative to click stop member housing 281, and capable of coaxial back and forth motion, between extended and retracted positions, relative to click stop member housing 281. Spring biased pin 282 cooperates with the plurality of detent apertures 235 of display rotational connector 230, permitting display rotational connector 230 and, in turn, display housing 210, to be maintained in any of several click-stop orientations, all perpendicular to the longitudinal axis of the camera, as display rotational connector 230 and, in turn, display housing 210, is rotated about the longitudinal axis.

In particular, spring biased pin 282, when in its extended position, will releasably lock display rotational connector 230 in a particular degree of rotation, upon engagement with an associated detent aperture 235. While the spring biasing pressure placed upon pin 282 and is sufficient to maintain rotational connector 230 in a particular detent orientation, the spring pressure is not so strong so as to preclude the application of manual rotational force on display rotational connector 230 from causing spring biased pin 282 to retract sufficiently to permit further rotation of the connector, towards rotating the overall video display to another detent orientation.

As can be seen from the foregoing, display 64 and display housing 210 of the present endoscopic camera may be positioned in a wide variety of orientations, by rotating the display housing about two different axes of rotation, as well as pivoting the display about a pivot point spaced distally from the camera housing's main body portion. First, display housing 210 may be rotated, transverse to the longitudinal axis of display swivel post 220, about a point P1 (FIG. 15) spaced from the main camera body and proximate swivel head portion 222 of display swivel post 220, by rotating swivel hinge pins 212 about swivel head portion 222. Second, display housing may be pivoted about point P1, from a first position wherein display housing 210 is substantially aligned with stem portion 221 and is substantially perpendicular to main body region 201, towards the camera body to a second position where at least a portion of the display housing contacts main body region 201. Third, by rotating display rotational connector 230, point P1 and display housing 210 may be rotated along an arc defining a portion of a circle concentric to the longitudinal axis of camera housing 200, passing through main body region 201, focus ring 44 and zoom ring 84.

For example, FIG. 28 shows the present endoscopic camera being held relatively close to the body and relatively high in the air during an endoscopic inspection. For convenient viewing of display 64, display housing 210 is rotated about point P1 (FIG. 15) to substantially align the display with the physician's head (not shown), so that the physician's body need not be shifted or neck be craned in order to readily view an image displayed during the endoscopic inspection.

Additional internal components of the present endoscopic camera are shown in FIGS. 20-21 as including battery 124, removable flash memory card 130, image acquisition device 140, primary printed circuit board 260, secondary printed circuit boards 261, 262 and 263, coupler mount 270, and coupler mount extension 271. Battery 124 is preferably a conventional lithium-ion type battery, which may be removed for recharging in a separate charging unit by first removing battery door 206 from camera housing 200. Alternatively, or in addition, a battery recharging jack may be disposed on the surface of housing 200, and a suitable recharging cradle or stand supplied, to permit the battery to be recharged in situ.

Removable flash memory card 130 preferably comprises an industry standard Secure Digital (SD) card, Mini SD card with SD card adapter, or MultiMedia card (MMC). Memory card 130 is releasably retained within an associated card slot, and may be removed from within the camera housing upon removal of the battery door.

Primary printed circuit board 260 includes much of the circuitry depicted in FIG. 13, including A/D converter 112, digital signal processor or microprocessor 120, controller 122, and on-board flash memory 132. Secondary printed circuit board 261 carries direction button 250, mode button 251, and menu button 252. Secondary printed circuit board 262 carries redundant video record button 253a and redundant still photograph shutter button 254a. Secondary printed circuit board 263 carries redundant video record button 253 and redundant still photograph shutter button 254.

Electrical conductors, such as ribbon cables or flexible circuits, connect image acquisition device 140, secondary printed circuit boards 261, 262 and 263, and high speed USB data I/O port 128 to primary printed circuit board 260. Camera body 200 may further contain a miniature microphone (not shown), also coupled to primary printed circuit board 260. In conjunction with on-screen menu functions provided via display 64 and processor 120, the microphone permits the physician to record sound clips, such as voice annotations, to the internal flash memory storage or the removable flash memory card, and to transfer such sound/voice clips to an external personal computer.

Although preferred embodiments of the invention have been illustrated in the accompanying Drawings and described in the foregoing Detailed Description, it will be understood that the invention is not limited to the embodiments disclosed, but is capable of numerous rearrangements, modifications, and substitutions of parts and elements without departing from the spirit of the invention. For example, it is also anticipated that the viewing screen on the camera may be a commercially available twin LCD display having a backlight and a system LSI (large-scale integrated circuit) chip between two LCD screens, allowing both sides of the display to work at the same time. Further, the system may include an audio input for accommodating stroboscopic analysis.

The invention claimed is:

1. A digital endoscopic camera adapted for interchangeable use with a variety of endoscopes having a first end and a second end, the first end having an eyepiece and the second end having a viewing end, the digital endoscopic camera comprising:
a housing having a main body portion having a longitudinal axis extending therethrough, an image acquisition device, a viewing screen operably mounted on the main body portion by a coupling, a coupler located at a distal end of the camera and removably connectable to an eyepiece of an attached endoscope, a processor, and memory with embedded software for processing data from the image acquisition device and for displaying an image on the viewing screen, the viewing screen being rotatable with respect to the main body portion along an arc, said coupling limiting a range of rotational motion along said arc to less 360 degrees.

2. The invention according to claim 1, wherein the viewing screen is further rotatable on the coupling about a point spaced from the main body portion of the digital endoscopic camera, the viewing screen remaining distally spaced from the main body portion during such rotation.

3. The invention according to claim 1, wherein the viewing screen is further pivotable on the coupling towards and away from the main body portion of the digital endoscopic camera about a point spaced from the main body portion.

4. The invention according to claim 1, wherein the viewing screen is further rotatable on the coupling about a point spaced from the main body portion of the digital endoscopic camera, the viewing screen remaining distally spaced from the main body portion during such rotation, and wherein the viewing screen is further pivotable towards and away from the main body portion of the digital endoscopic camera about the same point spaced from the main body portion of the digital endoscopic camera.

5. The invention according to claim 1, wherein the coupling comprises a rotating connector.

6. The invention according to claim 5, wherein the rotating connector rotates about the longitudinal axis of the housing.

7. The invention according to claim 6, wherein the viewing screen is mounted on the rotating connector via a post interposed between the viewing screen and the rotating connector, and wherein the viewing screen is capable of both rotatable and pivotal movement proximate a point of attachment of the viewing screen to the post.

8. A method of performing an endoscopic inspection, comprising the steps of:
providing a digital endoscopic camera adapted for interchangeable use with a variety of endoscopes having a first end and a second end, the first end having an eyepiece and the second end having a viewing end, the digital endoscopic camera comprising a housing having a main body portion having a longitudinal axis extending therethrough, an image acquisition device, a viewing screen operably attached to and mounted on the main body portion by a coupling, said coupling limiting a range of rotational motion along said arc to less 360 degrees, a coupler located at a distal end of the camera and removably connectable to an eyepiece of an attached endoscope, a processor, and memory with embedded software for processing data from the image acquisition device and for displaying an image on the viewing screen;
attaching an eyepiece of an endoscope to the coupler;
positioning a viewing end of the endoscope proximate a region to be displayed on the viewing screen; and
rotating the viewing screen relative to the main body portion along an arc.

9. The method according to claim 8, further comprising the step of rotating the viewing screen on the coupling about a point spaced from the main body portion of the digital endoscopic camera while maintaining the viewing screen in a distally spaced orientation, relative to the main body portion, during such rotation.

10. The method according to claim 9, further comprising the step of pivoting the viewing screen on the coupling about a point spaced from the main body portion of the digital endoscopic camera.

11. The method according to claim 9, further comprising the steps of:
rotating the viewing screen on the coupling about a point spaced from the main body portion of the digital endoscopic camera while maintaining the viewing screen in a distally spaced orientation, relative to the main body portion, during such rotation; and
pivoting the viewing screen on the coupling about the same point spaced from the main body portion of the digital endoscopic camera.

12. A digital endoscopic camera adapted for interchangeable use with a variety of endoscopes having a first end and a second end, the first end having an eyepiece and the second end having a viewing end, the digital endoscopic camera comprising:
a housing having a main body portion having a longitudinal axis extending therethrough, an image acquisition device, a viewing screen supported on the main body portion by a rotating coupling carried at least in part inside of the housing of the digital endoscopic camera, a coupler located at a distal end of the camera and removably connectable to an eyepiece of an attached endoscope, a processor, and memory with embedded software for processing data from the image acquisition device and for displaying an image on the viewing screen, the viewing screen being rotatable relative to the main body portion along an arc comprising at least a portion of a circle substantially concentric to the longitudinal axis of the main body portion of the digital endoscopic camera.

13. The invention according to claim 12, wherein the viewing screen is further rotatable about a point spaced from the main body portion of the digital endoscopic camera, the viewing screen remaining distally spaced from the main body portion during such rotation.

14. The invention according to claim 12, wherein the viewing screen is further pivotable towards and away from the main body portion of the digital endoscopic camera about a point spaced from the main body portion.

15. The invention according to claim 12, wherein the viewing screen is further rotatable about a point spaced from the main body portion of the digital endoscopic camera, wherein the viewing screen remaining distally spaced from the main body portion during such rotation, and wherein the viewing screen is further pivotable towards and away from the main body portion of the digital endoscopic camera about the same point spaced from the main body portion of the digital endoscopic camera.

16. The invention according to claim 12, wherein the rotating connector rotates relative to the main body portion about the longitudinal axis of the housing.

17. The invention according to claim 12, wherein the viewing screen is supported on the rotating connector via a post interposed between the viewing screen and the rotating connector, and wherein the viewing screen is capable of both rotatable and pivotal movement proximate a point of attachment of the viewing screen to the post.

18. The invention according to claim 12, wherein the viewing screen is supported on the rotating connector via a post interposed between the viewing screen and the rotating connector, the post being rotatable relative to the main body portion along an arc comprising at least a portion of a circle substantially concentric to the longitudinal axis of the main body portion of the digital endoscopic camera, and wherein the viewing screen is supported on the post to permit rotational movement about a post axis extending in a direction of elongation of the post.

19. The invention according to claim 12, wherein the viewing screen is supported on the rotating connector via a post interposed between the viewing screen and the rotating connector, the post being rotatable relative to the main body portion along an arc comprising at least a portion of a circle substantially concentric to the longitudinal axis of the main body portion of the digital endoscopic camera, and wherein the viewing screen is supported on the post to permit pivotable movement about a transverse axis extending orthogonally to a post axis extending in a direction of elongation of the post.

20. The invention according to claim 12, wherein the viewing screen is supported on the rotating connector via a post interposed between the viewing screen and the rotating connector, the post being rotatable relative to the main body portion along an arc comprising at least a portion of a circle substantially concentric to the longitudinal axis of the main body portion of the digital endoscopic camera, and wherein the viewing screen is supported on the post to permit both (i) rotational movement about a post axis extending orthogonally to the longitudinal axis, and (ii) pivotable movement about a transverse axis extending orthogonally to the post axis.

21. A digital endoscopic camera adapted for interchangeable use with a variety of endoscopes having a first end and a second end, the first end having an eyepiece and the second end having a viewing end, the digital endoscopic camera comprising:
a housing having a main body portion having a longitudinal axis extending therethrough, an image acquisition device, a viewing screen operably mounted on the main body portion by a coupling, at least a portion of said coupling being carried inside of said housing, a coupler located at a distal end of the camera and removably connectable to an eyepiece of an attached endoscope, a processor, and memory with embedded software for processing data from the image acquisition device and for displaying an image on the viewing screen, the viewing screen being rotatable with respect to the main body portion along an arc comprising at least a portion of a circle.

* * * * *